(12) United States Patent
Chen et al.

(10) Patent No.: US 10,815,302 B2
(45) Date of Patent: Oct. 27, 2020

(54) ANTI-PD-1 ANTIBODY AND USE THEREOF

(71) Applicants: Shanghai Junshi Biosciences Inc., Shanghai (CN); Junmeng Biosciences Co., Ltd., Suzhou (CN)

(72) Inventors: Bo Chen, Shanghai (CN); Hai Wu, Shanghai (CN); Hui Feng, Shanghai (CN)

(73) Assignees: Shanghai Junshi Biosciences Co., Ltd. (CN); Junmeng Biosciences Co., Ltd. (CN)

( * ) Notice: Subject to any disclaimer, the term of this patent is extended or adjusted under 35 U.S.C. 154(b) by 136 days.

(21) Appl. No.: 16/045,363

(22) Filed: Jul. 25, 2018

(65) Prior Publication Data
US 2019/0023782 A1    Jan. 24, 2019

Related U.S. Application Data

(63) Continuation of application No. 14/392,360, filed as application No. PCT/CN2014/072574 on Feb. 26, 2014, now Pat. No. 10,066,013.

(30) Foreign Application Priority Data

Jun. 26, 2013  (CN) .......................... 2013 1 0258289

(51) Int. Cl.
| A61K 39/00 | (2006.01) |
| C07K 16/28 | (2006.01) |
| A61K 39/395 | (2006.01) |
| C07K 14/705 | (2006.01) |

(52) U.S. Cl.
CPC ...... C07K 16/2803 (2013.01); C07K 16/2818 (2013.01); *A61K 39/39558* (2013.01); *A61K 2039/505* (2013.01); *C07K 14/705* (2013.01); *C07K 2317/21* (2013.01); *C07K 2317/24* (2013.01); *C07K 2317/33* (2013.01); *C07K 2317/565* (2013.01); *C07K 2317/70* (2013.01); *C07K 2317/76* (2013.01)

(58) Field of Classification Search
CPC .............................................. A61K 2039/505
See application file for complete search history.

(56) References Cited

U.S. PATENT DOCUMENTS

| 7,807,161 B2 | 10/2010 | Yamamoto et al. |
| 8,168,179 B2 | 5/2012 | Honjo et al. |
| 2016/0272708 A1 | 9/2016 | Chen et al. |

FOREIGN PATENT DOCUMENTS

| EP | 2172219 A1 | 4/2010 |
| EP | 2535354 A1 | 12/2012 |
| JP | 2006-340714 A | 12/2006 |
| WO | 2006/121168 A1 | 11/2006 |
| WO | 2008/156712 A1 | 12/2008 |
| WO | 2009/024531 A1 | 2/2009 |
| WO | 2010/029435 A1 | 3/2010 |
| WO | 2010/036959 A2 | 4/2010 |
| WO | 2011/110604 A1 | 9/2011 |
| WO | 2011/110621 A1 | 9/2011 |

OTHER PUBLICATIONS

Bergers, G. et al. "Extrinsic Regulators of Epithelial Tumor Progression: Metalloproteinases." *Current Opinion in Genetics and Development.* Published 2000. vol. 10. pp. 120-127.

Caldas, C. et al. "Humanization of the anti-CD18 antibody 6.7: An unexpected effect of a framework residue in binding to antigen." *Mol. Immunol.* Published May 2003. vol. 39, Issue 15. pp. 941-952.

Casset, F. et al. "A Peptide Mimetic of an Anti-CD4 Monoclonal Antibody by Rational Design." Biochem. Biophys. Res. Commun. Published Jul. 2003. vol. 307, Issue 1. pp. 198-205.

Chang, H. et al. "Loop-Sequence Features and Stability Determinants in Antibody Variable Domains by High-Throughput Experiments." *Structure.* Published Jan. 2014. vol. 22, Issue 1. pp. 9-21.

Chien, N. et al. "Significant Structural and Functional Change of an Antigen-Binding Site by a Distant Amino Acid Substitution: Proposal of a Structural Mechanism." *Proc. Natl. Acad. Sci. USA.* Published Jul. 1989. vol. 86, Issue 14. pp. 5532-5536.

De Pascalis, R. et al. Grafting of 'Abbreviated' Complementarity-Determining Regions Containing Specificity-Determining Residues Essential for Ligand Contact to Engineer a Less Immunogenic Humanized Monoclonal Antibody. *J. Immunol.* Published 2002. vol. 169, Issue 6. pp. 3076-3084.

Dennis, C. "Off by a Whisker." *Nature.* Published Aug. 7, 2006. vol. 442. pp. 739-741.

Extended European Search Report received in European Patent Application No. 14818708.1, filed Feb. 26, 2014. Received Jul. 14, 2017. 12 pages.

(Continued)

*Primary Examiner* — Stephen L Rawlings
(74) *Attorney, Agent, or Firm* — Kilpatrick Townsend & Stockton LLP

(57) ABSTRACT

This invention provides antibodies or functional fragments thereof that bind to PD-1 with high affinity. The invention provides nucleic acid molecules encoding the antibodies or the fragments thereof according to the present invention, expression vectors and host cells for expressing the antibodies or the functional fragments thereof according to the present invention, as well as methods for producing the antibodies or the functional fragments thereof according to the present invention. The present invention also provides immunoconjugates and pharmaceutical compositions comprising the antibodies or the functional fragments thereof according to the present invention. The present invention additionally provides methods for treating a plurality of diseases (comprising cancers, infectious diseases and inflammatory diseases) by using the antibodies or the functional fragments thereof disclosed herein.

11 Claims, 13 Drawing Sheets
Specification includes a Sequence Listing.

(56) References Cited

OTHER PUBLICATIONS

GenPept, Ig lambda chain V region—mouse, PIR: S52450, retrieved from www.ncbi.nlm.nih.gov/protein/552450 on Feb. 27, 2017, 2 pages.
Giusti, A. et al. "Somatic Diversification of S107 from an Antiphosphocholine to an Anti-DNA Autoantibody is Due to a Single Base Change in its Heavy Chain Variable Region." *Proc. Natl. Acad. Sci. USA*. Published May 1987. vol. 84, Issue 9. pp. 2926-2930.
Gura, T. "Systems for Identifying New Drugs Are Often Faulty." *Science*. Published Nov. 7, 1997. vol. 278, Issue 5340. pp. 1041-1042.
Gussow, D. et al. "Humanization of Monoclonal Antibodies." *Methods in Enzymology*. Published 1991. vol. 203. pp. 99-121.
Holm, P. et al. "Functional Mapping and Single Chain Construction of the Anti-Cytokeratin 8 Monoclonal Antibody TS1." *Mol. Immunol.* Published Feb. 2007. vol. 44, Issue 6. pp. 1075-1084.
International Application No. EP 14818709, Supplementary Partial European Search Report, dated Mar. 15, 2017, 6 pages.
International Application PCT/CN2014/072574, International Preliminary Report on Patentability dated Dec. 29, 2015, 17 pages.
International Application PCT/CN2014/072574, International Search Report and Written Opinion dated May 30, 2014, 20 pages.
Kelland, L.R. "'Of Mice and Men': Values and Liabilities of the Athymic Nude Mouse Model in Anticancer Drug Development." *Eur. J. Cancer*. Published Apr. 2004. vol. 40, Issue 6. pp. 827-836.
MacCallum, R. et al. "Antibody-antigen Interactions Contact Analysis and Binding Site Topography." *J. Mol. Biol.* Published Oct. 1996. vol. 262, Issue 5. pp. 732-745.
Mariuzza, R. et al. "The Structural Basis of Antigen-Antibody Recognition." *Ann. Rev. Biophys. Biophys. Chem.* 1987. vol. 16. pp. 139-159.
Peterson, J. K. et al. "Integrating Pharmacology and in vivo Cancer Models in Preclinical and Clinical Drug Development." *Eur. J. Cancer*. Published Jan. 2004. vol. 40. pp. 837-844.
Rudikoff, S. et al. "Single Amino Acid Substitution Altering Antigen-Binding Specificity." *Proc. Natl. Acad. Sci. USA*. Published 1982. vol. 79. pp. 1979-1983.
Saijo, N. "What Are the Reasons for Negative Phase III Trials of Molecular-Target-Based Drugs?" *Cancer Sci*. Published Oct. 2004. vol. 95, Issue 10. pp. 772-776.
Vajdos, F. et al. "Comprehensive Functional Maps of the Antigen-binding Site of an Anti-ErbB2 Antibody Obtained with Shotgun Scanning Mutagenesis." *J. Mol. Biol.* Published Jul. 2002. vol. 320, Issue 2. pp. 415-428.
Winkler, K. et al. Changing the Antigen Binding Specificity by Single Point Mutations of an Anti-p24 (HIV-1) Antibody. *Immunol*. Published Oct. 2000. vol. 165, Issue 8. pp. 4505-4514.
Wu, H et al. "Humanization of a Murine Monoclonal Antibody by Simultaneous Optimization of Framework and CDR Residues." *J. Mol. Biol.* Published Nov. 1999. vol. 294, Issue 1. pp. 151-162.
Yu, C. et al. "Rationalization and Design fo the Complementarity Determining Region Sequences in an Antibody-Antigen Recognition Interface." *PLoS One*. Published Mar. 2012. vol. 7, Issue 3. pp. 1-15.

|  |  | 1 | | | | | | | | | | | | | | | | | ↓ | | | | | | | | | | | | | | | | | | | | | | | | | | | | | | | 50 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human | (1) | M | Q | I | P | Q | A | P | W | P | V | V | W | A | V | L | Q | L | G | W | R | P | G | W | F | L | D | S | P | D | R | P | W | N | P | P | T | F | S | P | A | L | L | V | V | T | E | G | D | N | A |
| Cyno | (1) | M | Q | I | P | Q | A | P | W | P | V | V | W | A | V | L | Q | L | G | W | R | P | G | W | F | L | E | S | P | D | R | P | W | N | A | P | T | F | S | P | A | L | L | I | V | T | E | G | D | N | A |
| Mouse | (1) | M | W | V | R | Q | V | P | W | S | F | T | W | A | V | L | Q | L | S | W | Q | S | G | W | L | L | E | V | P | N | G | P | W | R | S | L | T | F | Y | P | A | W | L | T | V | S | E | G | A | M | A |

|  |  | 51 | | | | | | | | | | | | | | | | | | | | | | | | | | | | | | | | | | | | | | | | | | | | | | | | | 100 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human | (51) | T | F | T | C | S | F | S | N | T | S | E | S | F | V | L | N | W | Y | R | M | S | P | S | N | Q | T | D | K | L | A | A | F | P | E | D | R | S | Q | P | G | Q | D | C | R | F | R | V | T | Q | L |
| Cyno | (51) | T | F | T | C | S | F | S | N | A | S | E | S | F | V | L | N | W | Y | R | M | S | P | S | N | Q | T | D | K | L | A | A | F | P | E | D | R | S | Q | P | G | Q | D | C | R | F | R | V | T | Q | L |
| Mouse | (51) | T | F | T | C | S | L | S | N | W | S | E | S | L | M | L | N | W | N | Y | L | S | P | S | N | Q | T | E | L | Q | A | A | F | C | N | G | L | S | Q | P | V | Q | D | A | R | F | Q | I | I | Q | L |

|  |  | 101 | | | | | | | | | | | | | | | | | | | | | | | | | | | | | | | | | | | | | | | | | | | | | | | | | 150 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human | (101) | P | N | G | R | D | F | H | M | S | V | V | R | A | R | R | N | D | S | G | T | Y | L | C | G | A | I | S | L | A | P | K | A | Q | I | K | E | S | L | R | A | E | L | R | V | T | E | R | R | A | E |
| Cyno | (101) | P | N | G | R | D | F | H | M | S | V | V | R | A | R | R | N | D | S | G | T | Y | L | C | G | A | I | S | L | A | P | K | A | Q | I | K | E | S | L | R | A | E | L | R | V | T | E | R | R | A | E |
| Mouse | (101) | P | N | R | H | D | F | H | M | N | I | L | D | T | R | R | N | D | S | G | I | Y | L | C | G | A | I | S | L | H | P | K | A | K | I | E | E | S | P | G | A | E | L | V | V | T | E | E | I | L | E |

|  |  | 151 | | | | | | | | | | | | | | | ↓ | | | | | | | | | | | | | | | | | | | | | | | | | | | | | | | | | 200 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human | (151) | V | P | T | A | H | P | S | P | S | P | R | P | A | G | Q | F | Q | T | L | V | V | G | V | V | G | G | L | L | G | S | - | - | L | V | L | L | V | W | V | L | A | V | I | C | S | R | A | A | R | G |
| Cyno | (151) | V | P | T | A | H | P | S | P | S | P | R | P | A | G | Q | F | Q | A | L | V | V | G | V | V | G | G | L | L | G | S | - | - | L | V | L | L | V | W | V | L | A | V | I | C | S | R | A | A | Q | G |
| Mouse | (151) | T | S | T | R | Y | P | S | P | S | P | K | P | E | G | R | F | Q | G | M | V | I | G | I | M | S | A | L | V | G | I | P | V | L | L | L | L | A | W | A | L | A | V | F | C | S | T | S | M | S | E |

|  |  | 201 | | | | | | | | | | | | | | | | | | | | | | | | | | | | | | | | | | | | | | | | | | | | | | | | | 250 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Human | (199) | T | I | G | A | R | R | T | G | Q | P | L | K | E | D | P | S | A | V | P | V | F | S | V | D | Y | G | E | I | D | F | Q | W | R | E | K | T | P | E | P | P | V | P | C | V | P | E | Q | T | E | Y |
| Cyno | (199) | T | I | E | A | R | R | T | G | Q | P | L | K | E | D | P | S | A | V | P | V | F | S | V | D | Y | G | E | L | D | F | Q | W | R | E | K | T | P | E | P | P | A | P | C | V | P | E | Q | T | E | Y |
| Mouse | (201) | A | R | G | A | G | S | K | D | D | T | L | K | E | E | P | S | A | A | P | C | P | S | V | A | Y | E | E | L | D | F | G | G | R | E | K | T | P | E | L | P | T | A | C | V | - | - | H | T | E | Y |

|  |  | 251 | | | | | | | | | | | | | | | | | | | | | | | | | | | | | | | | | | | | 290 |
|---|---|---|---|---|---|---|---|---|---|---|---|---|---|---|---|---|---|---|---|---|---|---|---|---|---|---|---|---|---|---|---|---|---|---|---|---|---|
| Human | (249) | A | T | I | V | F | P | S | G | M | G | T | S | S | P | A | R | R | G | S | A | D | G | P | R | S | A | G | P | L | R | P | E | D | G | H | C | S | W | P | L |
| Cyno | (249) | A | T | I | V | F | P | S | G | L | G | T | S | S | P | A | R | R | G | S | A | D | G | P | R | S | P | R | P | L | R | P | E | D | G | H | C | S | W | P | L |
| Mouse | (249) | A | T | I | V | F | T | E | G | L | G | A | S | A | M | G | R | R | G | S | A | D | G | L | Q | G | P | R | P | P | R | H | R | D | G | H | C | S | W | P | L |

FIG. 9

ANTI-PD-1 ANTIBODY AND USE THEREOF

CROSS REFERENCE TO RELATED APPLICATIONS

This application is a continuation of Ser. No. 14/392,360, with a filing date of Jun. 7, 2016, now U.S. Pat. Ser. No. 10/066,013, which is a National Stage Entry of PCT/CN2014/072574, with a filing date of Feb. 26, 2014, which claims priority to Chinese Patent Application No. 201310258289.2, with a filing date of Jun. 26, 2013, all of which this application incorporates by reference herein.

REFERENCE TO SUBMISSION OF A SEQUENCE LISTING AS A TEXT FILE

The Sequence Listing written in file 098903-1097645-000110US_SequenceListing.txt created on Jul. 24, 2018, 32,644 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Technical Field

The present invention belongs to the field of biomedicine and relates to antibodies or functional fragments thereof that bind specifically to PD-1 with high affinity. The invention provides nucleic acid molecules encoding the antibodies or the fragments thereof according to the present invention, expression vectors and host cells for expressing the antibodies or the functional fragments thereof according to the present invention, as well as methods for producing the antibodies or the functional fragments thereof according to the present invention. The present invention also provides immunoconjugates and pharmaceutical compositions comprising the antibodies or the functional fragments thereof according to the present invention. The present invention additionally provides methods for treating a plurality of diseases (comprising cancers, infectious diseases and inflammatory diseases) by using the antibodies or the functional fragments thereof disclosed herein.

Description of Related Art

The programmed cell death 1 protein, PD-1, is a member of CD28 family and an immunosuppressive receptor expressed on the surfaces of the activated T cells and B cells (Yao, Zhu et al., Advances in targeting cell surface signaling molecules for immune modulation. *Nat Rev Drug Discov,* 2013, 12(2): 130-146). This receptor can bind to its ligands PD-L1 and PD-L2 to effectively reduce the immune response involving T cells. Tumor cells can escape the immune surveillance inside the body via high expression of PD-L1 (Okazaki and Honjo, PD-1 and PD-1 ligands: from discovery to clinical application. *International Immunology,* 2007, 19(7): 813-824 2007). The interaction between PD1 and PD-L1 can be blocked to significantly improve the tumor-killing activity of the CD8+ cytotoxic T cells.

PD-1 is primarily expressed on the surface of CD4+ T cells, CD8+ T cells, NKT cells, B cells, and the activated monocytes. The expression of PD-1 is primarily induced by the signals of T cell receptor (TCR) or B cell receptor (BCR). TNF can enhance the expression of PD-1 on the surfaces of these cells (Francisco, Sage et al., The PD-1 pathway in tolerance and autoimmunity. *Immunol Rev,* 2010, 236: 219-242). Human PD-1 is encoded by the gene Pdcd1, which is located on 2q37.3 and is 9.6 kb. It comprises five exons and four introns and its upstream comprises a promoter of 663 bp. The molecular structure of PD-1 comprises extracellular region, trans-membrane region and intracellular region. The amino acid sequences in the extracellular region has 24% homology with CTLA-4 and 28% homology with CD28. Its gene has primarily seven single-nucleotide polymorphic sites. The extracellular region comprises one structural domain of immuno-globulin variable IgV. The intracellular region comprises two signal transduction motifs based on tyrosine—ITIM (immunoreceptor tyrosine-based inhibitory motif) and ITSM (immunoreceptor tyrosine-based conversion motif). Once T cells are activated, PD-1 will associate with tyrosine phosphatase SHP2 primarily via the ITSM motif to cause the de-phosphorylation of the effector molecules including CD3ζ, PKCθ and ZAP70, etc.

There are two PD-1 ligands: PD-L1 and PD-L2. PD-L1 is also referred to as B7H1 or CD274 and PD-L2 is referred to as B7DC or CD273. The PD-L gene is located on the locus of 9p24.2 of human chromosome with a size of 42 kb. These ligands have 21-27% homology in amino acid sequence and structural similarity with B7-1, B7-2 and ICOSL. The PD-1 ligands all comprise one structural domain of immuno-globulin-like variable region, one constant-region-like structural domain, one trans-membrane region, and one short cytoplast tail. The cytoplast tail of PD-L1 is more conservative than that of PD-L2. PD-L1 and PD-L2 are expressed on different cell populations (Shimauchi, Kabashima et al., Augmented expression of programmed death-1 in both neoplastic and non-neoplastic CD4+ T cells in adult T cell leukemia/lymphoma. *Int J Cancer,* 2007, 121(12): 2585-2590). These cells include non-hematopoietic tissue and a variety of tumor types. PD-L1 is mainly expressed on T cells, B cells, dendritic cells, macrophages, mesenchymal stem cells and mast cells derived from bone marrow. PD-L1 is also expressed on the cells not derived from bone marrow, such as vascular endothelial cells, epithelial cells, skeletal muscle cells, hepatocytes, renal tubular epithelial cells, islet cells, brain astrocytes, and various types of non-lymphoid tumors such as melanoma, liver cancer, stomach cancer, renal cell carcinoma, as well as expressed on the cells at the immunologically privileged sites such as placenta, eyes. It has been suggested that PD-L1 can be extensive to some degree in regulating the auto-reactive T cells, B cells and immune tolerance and can play a role in response of peripheral tissue T cells and B cells. Nevertheless, the PD-L2 has very limited expressed region and exists only in macrophages and dendritic cells. PD-L1 is believed to play a role mainly in the immune presentation.

PD-1 and PD-L1 interact with each other to regulate and control the activation of T cells, which has been validated by much in tumors and viral infections. PD-L1 is expressed on the surfaces of various tumor cells which include lung cancer, liver cancer, ovarian cancer, cervical cancer, skin cancer, bladder cancer, colon cancer, breast cancer, glioma, renal carcinoma, stomach cancer, esophageal cancer, oral squamous cell cancer, and head/neck cancer. There are large amount of CD8+ T cells expressing PD-L1 found around these cancers. The clinical statistics reveal that the high level of expression of PD-L1 on cancer cells is related to the poor prognosis of cancer patients (Okazaki and Honjo 2007. *Supra.*).

Many chronic and acute viruses also escape the body's immune surveillance via the signals of PD-1 and PD-L1. For example, the expression level of PD-1 in HIV-infected patients is closely related to the degree of depletion of T cells and can be used as one of the markers of AIDS progression (Trabattoni, Saresella et al., B7-H1 is up-regulated in HIV infection and is a novel surrogate marker of disease progression. *Blood,* 2003, 101(7): 2514-2520). It is the same case for the patients diagnosed with chronic hepatitis B (Evans, Riva et al., Programmed death 1 expression during antiviral treatment of chronic hepatitis B: Impact of hepatitis B e-antigen seroconversion., *Hepatology,* 2008, 48(3): 759-769). The animal tests revealed that the mice whose PD-1 gene has been knocked out can control virus infection better than the normal mice; and hepatitis can be induced if the HBV-specific T cells are transferred into the HBV transgenic animals.

BRIEF SUMMARY OF THE INVENTION

The present invention relates to an anti-PD-1 antibody or a functional fragment thereof which can bind to the programmed cell death 1 (PD-1).

In one aspect, the antibody or the functional fragment thereof comprises a heavy chain CDR selected from the amino acid sequence SEQ ID NO: 1, 2, 3, 7, 8, 9, 13, 14, 15 or any variant of said sequence, and/or a light chain CDR selected from the amino acid sequence SEQ ID NO: 4, 5, 6, 10, 11, 12,16, 17, 18 or any variant of said sequence.

In some preferred embodiments, the antibody or the functional fragment thereof comprises a) heavy chain CDR1, CDR2 and CDR3 sequences selected from any of the following groups of various amino acid sequences or their variants:

|   | HCDR1 | HCDR2 | HCDR3 |
|---|-------|-------|-------|
| A | SEQ ID NO: 1 | SEQ ID NO: 2 | SEQ ID NO: 3 |
| B | SEQ ID NO: 7 | SEQ ID NO: 8 | SEQ ID NO: 9 |
| C | SEQ ID NO: 13 | SEQ ID NO: 14 | SEQ ID NO: 15 | and/or light chain CDR1, CDR2 and CDR3 sequences selected from any of the following groups of various amino acid sequences and their variants:

|   | LCDR1 | LCDR2 | LCDR3 |
|---|-------|-------|-------|
| A | SEQ ID NO: 4 | SEQ ID NO: 5 | SEQ ID NO: 6 |
| B | SEQ ID NO: 10 | SEQ ID NO: 11 | SEQ ID NO: 12 |
| C | SEQ ID NO: 16 | SEQ ID NO: 17 | SEQ ID NO: 18 |

In some preferred embodiments, the amino acid sequences of the heavy chain CDR1, CDR2 and CDR3 as well as the light chain CDR1, CDR2 and CDR3 of the antibody or the functional fragment thereof according to the present invention are selected from any of the following groups of various amino acid sequences or their variants:

|   | HCDR1 | HCDR2 | HCDR3 | LCDR1 | LCDR2 | LCDR3 |
|---|-------|-------|-------|-------|-------|-------|
| A | SEQ ID NO: 1 | SEQ ID NO: 2 | SEQ ID NO: 3 | SEQ ID NO: 4 | SEQ ID NO: 5 | SEQ ID NO: 6 |
| B | SEQ ID NO: 7 | SEQ ID NO: 8 | SEQ ID NO: 9 | SEQ ID NO: 10 | SEQ ID NO: 11 | SEQ ID NO: 12 |
| C | SEQ ID NO: 13 | SEQ ID NO: 14 | SEQ ID NO: 15 | SEQ ID NO: 16 | SEQ ID NO: 17 | SEQ ID NO: 18 |

In some embodiments, the antibody or the functional fragment thereof according to the present invention comprises a) a variable region of the heavy chain selected from the group consisting of amino acid sequences SEQ ID NOs: 19, 21, 23, and any variant of SEQ ID NO: 19, 21, or 23. and /or b) a variable region(s) of the light chain selected from the amino acid sequence SEQ ID NO: 20, 22, 24 or any variant of said sequence.

In one preferred embodiment, said variable region of the heavy chain is SEQ ID NO: 19 or any variant thereof and said light chain is SEQ ID NO: 20 or any variant thereof.

In another preferred embodiment, said variable region of the heavy chain is SEQ ID NO: 21 or its variant and said variable region of the light chain is SEQ ID NO: 22 or any variant thereof.

In another more preferred embodiment, said variable region of the heavy chain is SEQ ID NO: 23 or any variant thereof and said variable region of the light chain is SEQ ID NO: 24 or any variant thereof.

The antibody or the functional fragment thereof according to the present invention can be a chimeric antibody, a humanized antibody or a fully human antibody.

The antibody or the functional fragment thereof according to the present invention can be humanized. Methods of preparing humanized antibody are generally known by the skilled in the art. For example, the CDR sequence according to the present invention can be transferred into the variable region of a human antibody to prepare the humanized anti-PD-1 antibody of the present invention. Said humanized antibody will not produce anti antibody response (AAR) and human anti-mouse antibody (HAMA) response, and will not be removed quickly due to neutralization by anti antibody and will play a role of immunological effect such as ADCC and CDC effects.

In some preferred embodiments, the humanized PD-1 antibody or the functional fragment thereof according to the present invention comprises a) a variable region of the heavy chain selected from the group consisting of amino acid sequences SEQ ID NO: 33, 35, 36 and any variant of SEQ ID NO: 33, 35, or 36, and/or b) a variable region of the light chain selected from SEQ ID NO: 34, 37 and any variant of SEQ ID NO: 34 or 37.

In one preferred embodiment of the humanized antibody or the functional fragment thereof according to the present invention, said variable region of the heavy chain is SEQ ID NO: 33 or its variant and said variable region of the light chain is SEQ ID NO: 34 or its variant.

In another preferred embodiment of the humanized antibody or the functional fragment thereof according to the present invention, said variable region of the heavy chain is SEQ ID NO: 35 or its variant and said variable regions of the light chain is SEQ ID NO: 34 or its variant.

In another preferred embodiment of the humanized antibody or the functional fragment thereof according to the present invention, said variable region of the heavy chain is SEQ ID NO: 36 or its variant and said variable region of the light chain is SEQ ID NO: 34 or its variant.

In another more preferred embodiment of the humanized antibody or the functional fragments thereof according to the present invention, said variable region of the heavy chain is SEQ ID NO: 35 or its variant and said variable region of the light chain is SEQ ID NO: 37 or its variant.

The present invention also provides a separate nucleic acid molecule encoding the antibody or the functional fragment thereof according to the present invention. In one preferred embodiment, said nucleic acid molecule comprises the nucleotide sequence as shown by any of SEQ ID NO: 25-30, 38-42 or any combination thereof.

The present invention also provides an expression vector comprising said nucleic acid molecule as well as a host cell comprising said expression vector.

The present invention provides methods of producing anti-PD-1 antibodies or the functional fragments thereof, which comprises: culturing said host cells according to the present invention under the condition of allowing it to produce said antibodies or the functional fragments thereof, as well as recovering said antibodies or the functional fragments thereof produced in this way.

In another aspect, the present invention relates to an immunoconjugate comprising the antibody or the functional fragment according to the present invention that conjugates with a therapeutic agent. Said therapeutic agent is preferably toxin, radioisotope, drug or cytotoxic agent.

The present invention also relates to a pharmaceutical composition comprising the antibody or the functional fragment thereof according to present invention as well as a pharmaceutical carrier.

On the other hand, the present invention provides a method used to prevent or treat diseases or conditions through removing, inhibiting or lowering the activity of PD-1, which comprises administration of an effective treatment dose of the antibody or the functional fragment thereof according to the present invention, nucleic acid, expression vector, host cell, immunoconjugate or pharmaceutical composition to a subject in need, wherein: said diseases or conditions are selected from the group consisting of cancers, infectious diseases and inflammatory diseases. Said cancers are preferably selected from the group consisting of melanoma, renal cancer, prostate cancer, breast cancer, colon cancer, lung cancer, bone cancer, pancreatic cancer, skin cancer, head or neck cancer, cutaneous or intraocular malignant melanoma, uterine cancer, ovarian cancer, rectal cancer, anal region cancer, stomach cancer, testicular cancer, uterine cancer, fallopian tube cancer, endometrial cancer, cervical cancer, vaginal cancer, vulva cancer, Hodgkin's disease, non-Hodgkin's lymphoma, esophagus cancer, small intestinal cancer, cancer of endocrine system, thyroid cancer, parathyroid cancer, adrenal cancer, soft tissue sarcoma, urethra cancer, penile cancer, chronic or acute leukemia which includes acute myeloid leukemia, chronic myeloid leukemia, acute lymphoblastic leukemia, chronic lymphocytic leukemia, solid tumors during childhood, lymphocytic lymphoma, bladder cancer, kidney or ureter cancer, renal pelvis cancer, vegetation of central nervous system, primary central nervous system lymphoma, tumor angiogenesis, spinal axis tumors, brain stem glioma, pituitary adenoma, Kaposi's sarcoma, epidermoid carcinoma, squamous cell cancer, T cell lymphoma, environmentally induced cancers which include those induced by asbestos and the combination of said cancers, said infectious diseases are preferably selected from HIV, influenza, herpes, giardiasis, malaria, leishmaniasis, pathogenic infections caused by the following viruses: hepatitis viruses (hepatitis A, B and C), herpes virus (such as VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papilloma virus, molluscum virus, polio virus, rabies virus, JC virus and arboviral encephalitis virus, pathogenic infections by the following bacteria: chlamydia, rickettsia, mycobacteria, staphylococcus, streptococcus, pneumococcus, meningococcus and conococci, klebsiella, proteus, serratia, pseudomonas, legionella, diphtheria, salmonella, tuberculosis, cholera, tetanus, botulism, anthrax, plague, leptospirosis and Lyme disease bacteria, pathogenic infections by the following fungi: Candida (Candida albicans, Candida krusei, Candida glabrata, Candida tropicalis, etc.), Cryptococcus neoformans, aspergillus (Fumigatus, Aspergillus niger, etc.), genus of Mucor (mucor, absidia, rhizopus), Sporothrix schenckii, dermatitis yeast bud, paracoccidiodes brasiliensis, Coccidioides immitis and Histoplasma capsulatum, pathogenic infections by the following parasites: Entamoeba histolytica, Colon balantidium, fernando's worms, amoeba spine, suction blow Giardia, cryptosporidium, Pneumocystis carinii, P. vivax, voles Babesia, Trypanosoma brucei, Cruz trypanosoma, Leishmania donovani, Toxoplasma gondii and Nippostrongylus brasiliensis, said inflammatory diseases are preferably selected from acute disseminated encephalomyelitis, Addison's disease, ankylosing spondylitis, antiphospholipid antibody syndrome, autoimmune hemolytic anemia, autoimmune hepatitis, arthritis, Behcet's disease, bullous blistering day sores, celiac disease, Chagas disease, Crohn's disease, dermatomyositis, type-1 diabetes, pulmonary hemorrhage—nephritic syndrome, graft versus host disease, Graves' disease, Guillain—Barre syndrome, Hashimoto's disease, hyperimmunoglobulin E syndrome, idiopathic thrombocytopenic purpura, lupus erythematosus, multiple sclerosis, myasthenia gravis, pemphigus, pernicious anemia, polymyositis, primary biliary cirrhosis, psoriasis disease, rheumatoid arthritis, Sjogren's syndrome, temporal arteritis, vasculitis, and Wegener's granulomatosis.

The present invention also provides the uses of the antibody or the functional fragment thereof according to the present invention, nucleic acid, expression vector, host cell, immunoconjugate or pharmaceutical composition in preparing the drugs for treating the diseases or conditions.

BRIEF DESCRIPTION OF THE SEVERAL VIEWS OF THE DRAWINGS

FIG. 9 shows the comparison between the PD-1 sequences of human (SEQ ID NO.43), *Macaca fascicularis* (Cyno) (SEQ ID NO.44) and mouse (SEQ ID NO.45), wherein the major differences between the mouse PD-1 protein and the human/*Macaca fascicularis* PD-1 protein are boxed.

DETAILED DESCRIPTION OF THE INVENTION

Figure 1:
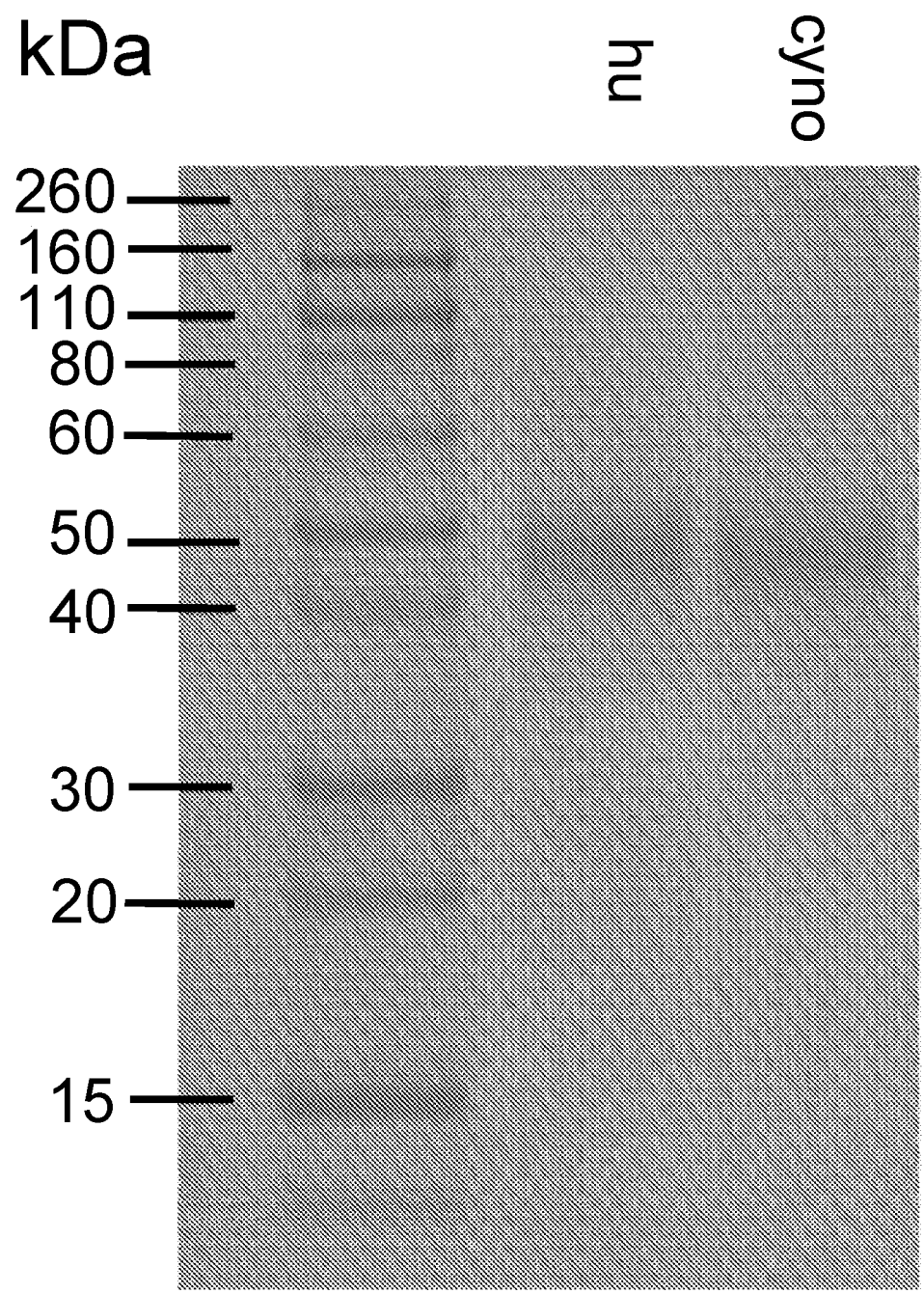
FIG. 1 shows the protein size of the extracellular structural region of PD-1 derived from human (hu) and *Macaca fascicularis* (cyno) as indicated by SDS-PAGE.

Unless otherwise defined, all the technical terms used in this patent have the same meanings understandable by the ordinary technicians in the art. As for the definitions and terms in the art, the professionals can specifically refer to Current Protocols in Molecular Biology (Ausubel). The abbreviation of amino acid residues employs a form of the standard code of 3 letters and/or 1 letter used in the field for each of the 20 commonly-used L-amino acids.

The present invention provides an anti-PD-1 antibody and a functional fragment thereof, which can bind to the programmed cell death 1 (PD-1). The antibody and the functional fragment thereof according to the present invention has at least one of the following features: the ability to block the interaction between PD-1 and PD-L1 via high affinity, or bind to PD-1 with high specificity but not to other CD28 family members (such as ICOS, CTLA-4 and CD28), or activate tumor-specific T cells to kill the tumor cells and promote CD8+ to enter the tissue of solid tumor so as to increase greatly the levels of the immune effectors such as IFNγ.

The present invention also provides a humanized anti-PD-1 antibody and a functional fragment thereof. Said humanized antibody is obtained by computer simulation design of the mouse-derived antibody produced by immunized mouse in combination with bacteriophage display technology. Its binding epitopes are also identified accordingly based on its binding characteristics with PD-1 proteins of various species. Except the advantageous characteristics of the anti-PD-1 antibody and the functional fragment thereof described above, said humanized anti-PD-1 antibody and the functional fragment thereof according to the present invention also binds to PD-1 proteins of human or *Macaca fascicularis* via high affinity, but does not interact with the mouse-derived PD-1 protein.

On the premise of not substantially influencing the activity of the antibody, those skilled in the art can replace, add and/or remove one or more (such as 1, 2, 3, 4, 5, 6, 7, 9 or 10 or more) amino acids of the sequence according to the present invention so as to produce a variant of the sequence of said antibody or the functional fragment thereof. They are all deemed to be included in the protection scope of the present invention. For example, the amino acid in the variable region can be replaced with that of similar property. The sequence of said variant according to the present invention can have an identity of at least 95%, 96%, 97%, 98% or 99% to its source sequence. Said sequence identity described in the present invention can be measured by sequence analysis software, for example, the computer program BLAST using default parameter, especially BLASTP or TBLASTN.

The antibody according to the present invention can be full length (for example, IgG1 or IgG4 antibody) or comprises only the part that binds an antigen (for example, Fab, F(ab')2 or scFv fragment), or an antibody that has been modified to affect its function. The present invention comprises the anti-PD-1 antibody comprising modified glycosylation pattern. In some applications, it is useful to conduct modification to remove the undesirable glycosylation sites or avoid the part of fucose on the oligosaccharide chain to, for example, enhance the antibody of antibody-dependent cellular cytotoxicity (ADCC) function. In some other applications, the modification of galactosylation can be conducted to change the complement-dependent cytotoxcity (CDC).

The terms used in this patent—"functional fragment" refers to especially the antibody fragment such as Fv, scFv (sc refers to single strand), Fab, F(ab')2, Fab', scFv-Fc fragment or diabody, or any fragment whose half life should be possibly increased by means of chemical modification or incorporating into the liposome. Said chemical modification is, for example, adding polyalkylene glycol such as polyethylene glycol ("pegylation, PEGylated") (referred to as a pegylated fragment such as Fv-PEG, scFv-PEG, Fab-PEG; F(ab')2-PEG or Fab'-PEG) ("PEG" is polyalkylene glycol) and said fragment has EGFR binding activity. Preferably, said functional fragment comprises a partial sequence of the heavy or light variable chain of their source antibody. Said partial sequence maintains sufficient antigen-binding specificity and affinity, which are the same as those of its source antibody. As for PD-1, the affinity is preferably at least 1/100, and more preferably at least 1/10, of the affinity of its source antibody. Said functional fragment comprises at least 5 amino acids and preferably comprises 10, 15, 25, 50 and 100 continuous amino acids of its source antibody sequence.

Technicians skilled in the art can clone the DNA molecule encoding said anti-PD-1 antibody according to the present invention into a vector and then transform to host cell. In this way, the present invention can also provide a type of recombinant DNA vector, which comprises a DNA molecule encoding said anti-PD-1 antibody according to the present invention.

Preferably, said recombinant DNA vector is a type of expression vector. Technicians skilled in the art can clone the DNA molecule of said antibody into the expression vector and transform it into host cell to get antibody by means of induction expression. The expression vector according to the present invention comprises the encoding DNA sequence of the variable region of the heavy chain, the variable region of the light chain and/or constant region of the anti-PD-1 antibody. Nevertheless, two types of expression vectors can also be constructed separately: one comprising the variable region of the heavy chain and constant region and another comprising the variable region of the light chain and constant region. The two types of expression vectors are then introduced into the same mammal. In one preferred embodiment, said expression vector further comprises a promoter and a DNA sequence encoding the secreting signal peptide as well as at least one type of drug-resistant gene used to screen.

The host cells according to the present invention can be prokaryotic host cell, eukaryotic host cell or bacteriophage. Said prokaryotic host cell can be *Escherichia coli, Bacillus subtilis, Streptomyces* or *Proteus mirabilis*, etc. Said eukaryotic host cell can be fungi such as *Pichia pastoris, Saccharomyces cerevisiae,* fission yeast and *Trichoderma,* insect cells such as *Spodoptera frugiperda,* plant cells such as tobacco, mammalian cells such as BHK cell, CHO cell, COS cell and myeloma cell. In some embodiments, the host cells according to the present invention are preferably mammalian cells, more preferably, BHK cells, CHO cells, NSO cells or COS cells.

The term "pharmaceutical composition" used herein refers to the combination of at least one kind of drug and randomly selected pharmaceutical carriers or excipients for a special purpose. In some embodiments, said pharmaceutical composition includes the combinations, which are separated in time and/or space provided that they can function synergistically to realize the purpose of the present invention. For example, the ingredients contained in said pharmaceutical composition (for example, the antibody, nucleic acid molecule, combination and/or conjugate of nucleic acid molecule) can be administered to the subject as a whole or separately. In the case that the ingredients contained in said pharmaceutical composition are administered separately to the subject, they can be used simultaneously or in turn. Preferably, said pharmaceutical carrier is water, buffer aqueous solution, isotonic saline solutions such as PBS (phosphate buffer), glucose, mannitol, dextrose, lactose, starch, magnesium stearate, cellulose, magnesium carbonate, 0.3% glycerol, hyaluronic acid, ethanol or polyalkylene glycols such as polypropylene glycol, triglyceride and others. The type of the pharmaceutical carrier can be selected based on whether the composition according to the present invention is formulated to be administered via oral, intranasal, intradermal, subcutaneous, intramuscular or intravenous route. The composition according to the present invention can comprise a wetting agent, an emulsifier or a buffer solution as additive.

The pharmaceutical composition according to the present invention can be administered via any appropriate route, for example, oral, intranasal, intradermal, subcutaneous, intramuscular or intravenous.

In one relevant aspect, the present invention provides a pharmaceutical composition comprising an anti-PD-1 antibody and a second therapeutic agent. In one embodiment, the second therapeutic agent is any agent advantageous to combine with anti-PD-1 antibody. Examples of such agent advantageous to combine with anti-PD-1 antibody include, but are not limited to, other agents that can inhibit the activity of PD-1 (including the fragments, the peptide inhibitor, the small molecule antagonists, etc., binding to other antibodies or antigens) and/or the agents that can interfere with the transduction of upstream or downstream signals of PD-1.

The terms "prevent or treat diseases or conditions through removing, inhibiting or lowering the activity of PD-1" refers to the diseases or conditions caused by expression of PD-1 or those diseases or conditions with the symptoms/features of PD-1 expression. In some embodiments, said diseases or conditions are cancers or infectious diseases. Said cancers include, but are not limited to, lung cancer, liver cancer, ovarian cancer, cervical cancer, skin cancer, bladder cancer, colon cancer, breast cancer, glioma, renal cancer, gastric cancer, esophageal cancer, oral squamous cell carcinoma, head/neck cancer. Said infectious diseases include, but are not limited to, HIV infection and Hepatitis B virus infection.

The term "effective treatment dose" used in this patent refers to a dose sufficient to confer benefit to the application target. The dose administered, the administration rate and the duration may depend on the conditions and severity of the target to treat. The prescription of treatment (for example, determination of dose) is determined by a physician, who may consider the factors such as the disease to treat, the condition of individual patient, the administration site, and the administration method.

The term "subject" used in this patent refers to mammals such as human or other animals, for example, wild animals (heron, stork, crane, etc), livestock (duck, goose, etc) or laboratory animals (orangutan, monkey, rate, mouse, rabbit and guinea pig, etc)

The following Examples are provided to prove and further explain some preferred embodiments according to the present invention. Nevertheless, they should not be interpreted as limiting the scope of the present invention.

EXAMPLES

Example 1

Clone Human PD1 Extracellular Structural Region into Eukaryotic Expression Plasmid Total RNA from human peripheral blood cells (Beijing Red Cross Blood Center) was extracted with TRIzol™ RNA extraction kit (Invitrogen) and cDNA was obtained with reverse transcription kit by Invitrogen. The PD1 extracellular fragment was obtained by PCR amplification of the cDNA using the upstream primer 5'-GTACGCTAGCCAC-CATGCAGATCCCACAGGC-'3 (SEQ ID NO.31) and the downstream primer 5'-GATCCTCGAGCCACCA-GGGTTTGGAACTG-'3 (SEQ ID NO.32),. The amplified product was digested by Nhe I and Xho I and cloned into the eukaryotic expression plasmid system of pCDNA3.1. 293T cells (ATCC) were transfected with this plasmid for 3 days, the supernatant of the cell culture was collected to purify h-PD1. Total RNA from the peripheral blood cells of *Macaca fascicularis* were also extracted and the produced cDNA was cloned into the a eukaryotic expression vector.

As shown in FIG. 1, due to the posttranslational modification such as glycosylation, the protein sizes of PD-1 extracellular structural regions of human-derived (hu) and *Macaca fascicularis* derived (cyno) PD-1 were about 50K Dalton after Coomassie blue staining.

Example 2

Test the Combination of the PD-1 on Cells and the Ligand PD-L1

1. Isolate T Cells from Human Peripheral Blood Cells

When the suspension of peripheral blood cells (Beijing Blood Institute) flows through nylon-fiber column (Beijing Hede Biotechnology Company), the B cells, plasma cells, mononuclear cells and some ancillary cells will adhere selectively to the nylon fiber although most T cells pass through nylon-fiber column and hence yield the enriched T cell population. The procedure is simply described as follows: take a 50-ml glass syringe, pull out the syringe core and fit a rubber hose with clip into the syringe nozzle. Tie up some nylon fibers and insert them into the syringe. Fix the syringe on the support and pour RPMI cell culture fluid at 37° C. to pre-treat the nylon fibers. Close the valve, open the valve after 0.5 hours to release the cell culture fluid. Dilute the cell fluid to be separated with pre-heated RPMI culture fluid to an appropriate concentration about $5.00 \times 10^7$ cells/ml. Pour the cell fluid into the syringe and submerge the nylon-fiber column. Cover the syringe and incubate at 37° C. for 1 hour. Open the lower opening, release the fluid slowly (1 drip/min) and collect in a centrifuge tube. Centrifuge at 1000×g for 10 minutes to yield the desired T lymphocytes.

2. Conjugate rh-PD-L1 Recombinant Protein with Biotin

Mix 100 ug rh-PD-L1 recombinant protein (purchased from Beijing Sino Biological Inc.) with the biotin-amino-caproic acid-NETS (Thermo) dissolved in DMSO at a molar ratio of 1:4 and keep the mixture still at room temperature for 1 hour. Then pass the reaction mixture through G25 gel column (Thermo) to separate the biotin—marked rh-PD-L1 and the free biotins.

Figure 2:
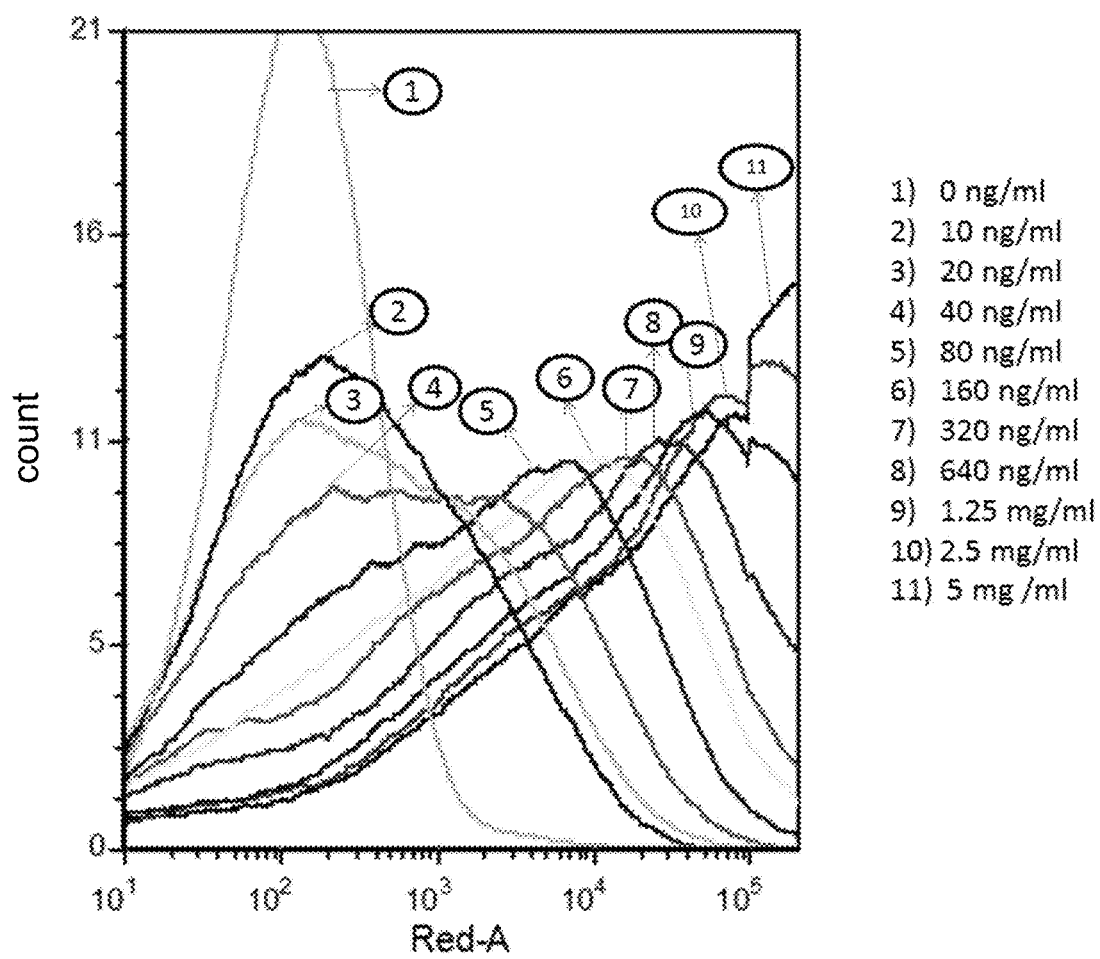
FIG. 2 shows the combination of biotin-labeled rh-PD-L1 and human T cells measured by flow cytometry.

3. Combine the Biotin-marked rh-PD-L1 with Human T Cells rh-PD-L1 recombinant protein conjugated with different concentrations of biotins was mixed with $10^5$ T cells isolated according to the method above. The mixture was incubated at 4° C. for 15 minutes. After washing three times with PBS, a streptavidin-allophycocyanin (Thermo) (SA-APC) to 0.2 ug/ml was added and incubated with the mixture at 4° C. for 20 minutes. After washing three more times with PBS, samples were measured at 660 nm using the Beckman Dickson FACSCalibur. As shown in FIG. 2, the result shows that the PD-L1 protein conjugated with biotin can bind to T cells.

Example 3

Preparation of Anti rh-PD-1 Antibody

1. Animal Immunization 10 ug rh-PD-1 recombinant protein of 1mg/ml as antigen was mixed with equivalent immune adjuvants (Freund adjuvant (Sigma—Aldrich)) and immunized subcutaneously three female FVB mice of 6-week old. After the first immunization, the same dose is administered once per week to boost the immunization.

2. Cell Fusion

After the last shot of enhanced immunization, lymph nodes at the thigh root of mice were collected and milled in the normal saline. The produced suspension, enriched with B cells, was fused with the SP2/0 cells via the conventional method of electrophoretic transfer (see BTX electroporator manual). The fusion cells were cultured at the condition of 5% $CO_2$ and 37° C. in the RPMI-1640 whole culture medium containing HAT (Sigma) to culture.

Example 4

Experiment of Blocking Ligand and Receptor

From 20000 of monoclonal hybridoma cell lines, the enzyme label (Elisa) reaction was employed to screen out the 1220 clones of secreted antibodies, which can bind to PD-1 proteins. Five of these 1220 clones of antibodies had the ability to inhibit the binding between the biotin-marked PD-L1 and the PD-1 receptor on T cells to various degrees.

1 ug/ml of each of the five antibodies described as above were incubated with 312 ng/ml of biotin-marked rh-PD-L1 (concentration) at room temperature for 20 minutes. The mixture was then incubated with T cells isolated from human peripheral blood cells at 4° C. for 15 minutes. After washing three times with normal saline and 0.2 ug/ml of SA-APC was added to the mixture and incubated at 4° C. for 15 minutes. After washing three times with normal saline, samples were measured with BD's flow cytometer to verify whether the antibodies can inhibit the binding of rh-PD-L1 and PD-1 receptor on the surface of T cell.

Figure 3:
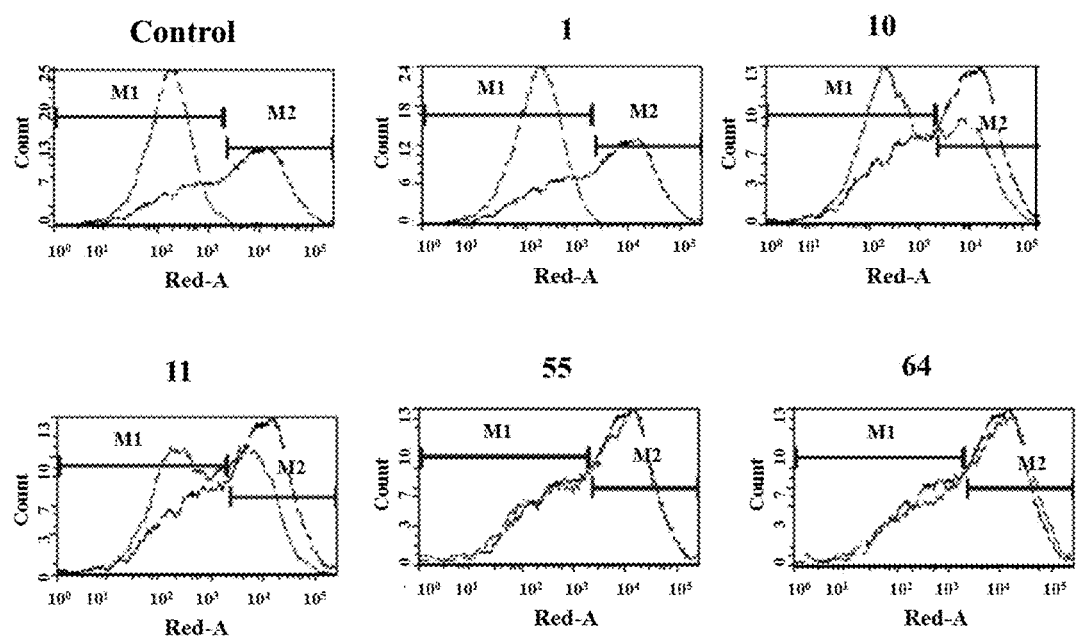
FIG. 3 shows that the PD-L1 control, Clone 1, 10, 11, 55 and 64 block the binding between the PD-1 on cell surface with the ligand PD-L1 as measured by flow cytometry.

As shown in FIG. 3, Clones 1, 10 and 11 can block the binding of PD-1 with the ligand PD-L1 on the cell surface, whereas Clones 55 and 64 can only play a weak inhibition role.

Example 5

Binding of the Antibody Candidates to Other CD28 Family Members

In order to further test the binding specificity of antibody candidate Clones 1, 10, 11, 55 and 64, 1 ug/ml of rh-PD-1 or the other CD28 family members, i.e., ICOS, CTLA-4 and CD28 (R&D System) in the carbonate buffer solution (0.05M PH9) was used to coat a 96-well enzyme-label plate and kept at 4° C. overnight. The next day, solution was removed from the wells and the wells were washed three times with a washing buffer (PBS+0.5% TWEEN). PBS solution containing 3% BSA was added to the wells to block for 20 minutes. After washing three times with the washing buffer, 100 ul of each antibody clone was added at 1 ug/ml and incubated at room temperature for 1 hour. After three washes with the washing buffer, HRP cross-linked goat anti mouse antibody (Jackson Immunoresearch) was diluted in the washing buffer 1: 0000, and added to the sample wells and incubated at room temperature for 1 hour. After three washes with the washing buffer, 50 ul TMB (tetramethyl benzidine) substrate solution was added to develop the color. The color reaction was terminated after the reaction was continued for 10 minutes at room temperature by adding 25 ul of 0.5M sulfuric acid solution to the reaction mixture. The absorbance was then measured at 450 nm.

Figure 4:
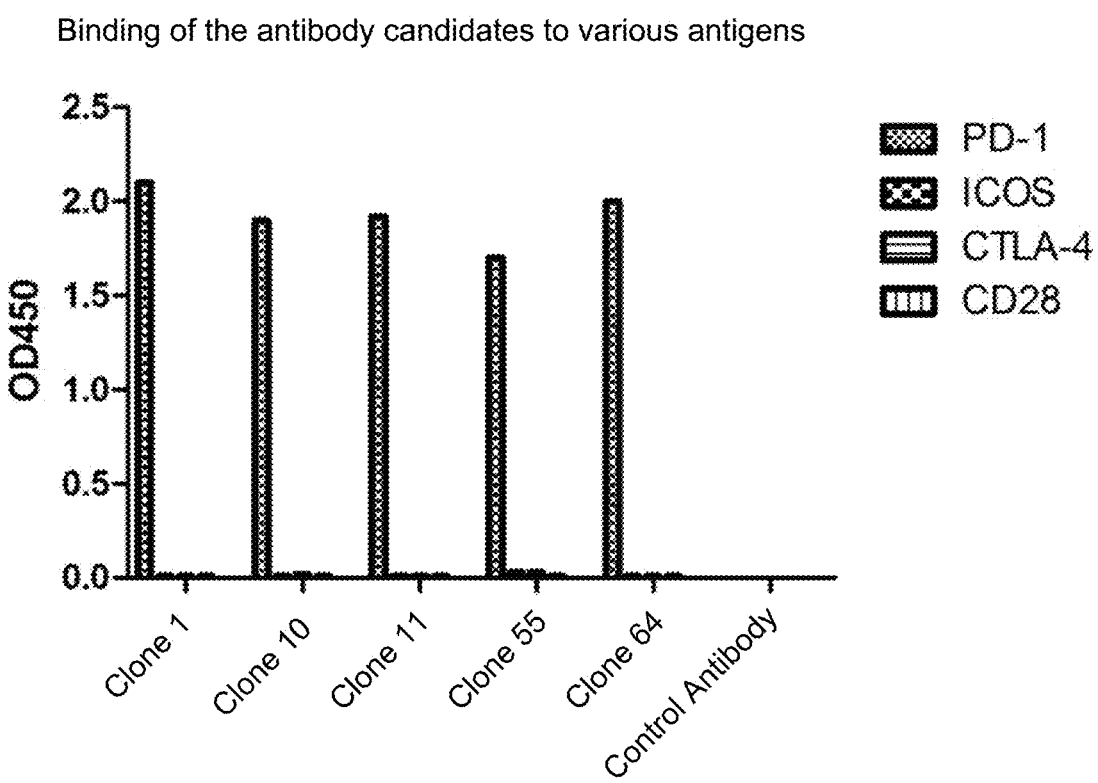
FIG. 4 shows the binding of the antibody control, Clone 1, 10, 11, 55 and 64 with the PD-1 as well as other CD28 family members (ICOS, CTLA-4 and CD28).

As shown in FIG. 4, all the antibody candidate clones tested can recognize and bind to rh-PD-1 but not other CD28 family members. Example 6. The variable region sequence of the antibody candidates Candidate hybridoma cells were cultured until reaching a total count of $10^7$. The cells were collected by centrifugation at 1000 rpm for 10 minutes and total RNA from the cells was extracted with TRIzol™ reagent kit (Invitrogen). The total RNA was used as the template to synthesize the first strand cDNA (Qiagen), which, in turn, was used as a template to amplify the DNA sequence of the variable region of the respective hybridoma cells. The primer sequence used in the amplification reaction is complementary to the first framework region and the constant region of the variable region of antibody (Larrick, J. W., et al., (1990) Scand. J. Immunol., 32, 121-128 and Coloma, J. J. et al., (1991) BioTechniques, 11,152-156 et al.). In a 50 µl reaction system, 1 µl of cDNA, 5 µl of 10×PCR buffer solution, each 1 µl (25 pmol) of upstream and downstream primer, 1 µl of dNTP, 1 µl of 25 mmol/L $MgCl_2$, 39 µl of $H_2O$, were added separately. The initial denaturation of the template was conducted at 95° C. for 10 minutes. 1 µl of Taq enzyme (Invitrogen) was added to the reaction to start temperature cycles of the PCR amplification. The reaction conditions are as follows: denaturing at 94° C. for 1 minute, annealing at 58° C. for 1 minute, and extending at 72° C. for 115 minutes. The cycle was repeated 30 times before the reaction mixture was kept at 72° C. for 10 minutes.

The amplified product is sequenced and the sequences of variable regions of the heavy chain and light chain of Clone 1, 10 and 11 of hybridoma are shown below:

```
Clone 1:
Heavy chain (SEQ ID NO. 19)
<------------FR1-------------> CDR1  <----FR2----> CDR2
QGQLQQSGAELVRPGASVTLTCKASGYTFTDYEMHWVKQTPIHGLEWIGVIESETGGTAYNQKFKG
<--------------FR3-------------->     CDR3       <---FR4--->
KAKLTADKSSSTAYMELRSLTSEDSAVYYCTREGITTVATTYYWYFDVWGTGTTVTSS
```

```
Nucleic acid sequence (SEQ ID NO. 25)
CAGGGTCAACTGCAGCAGTCTGGGGCTGAGCTGGTGAGGCCTGGGGCTTCAG
TGACGGTGACCTGCAAGGCTTCGGGCTACACATTTACTGACTATGAAATGCACT
GGGTGAAGCAGACACCTATACATGGCCTGGAATGGATTGGAGTTATTGAATCTG
AAACTGGTGGTACTGCCTACAATCAGAAGTTCAAGGGCAAGGCCAAACTGACT
GCAGACAAATCCTCCAGCACAGCCTACATGGAGCTCCGCAGCCTGACATCTGA
GGACTCTGCCGTCTATTACTGTACAAGAGAGGGTATTACTACGGTAGCAACTAC
GTACTACTGGTACTTCGATGTCTGGGGCACAGGGACCACGGTCACCGTCTCCTC
A Light chain (SEQ ID NO. 20)
<--------FR1--------->        CDR1        <-----FR2---->    CDR2
DVLMTQTPLSLPVSLGDQASISCRSSQSIVHSNGNTYLEWLQKPGQSPELLIYKVYNRFS
<-------------FR3--------------->        CDR2      <--FR4-->
GVPDRFSGSGSGTDFTLKISRVEAEDLGVYYCFQGSHVPFTFGSGTKLEIK Nucleic acid sequence (SEQ ID NO. 26)
GATGTTTTGATGACCCAGACTCCACTCTCCCTGCCTGTCAGTCTTGGAGATCAA
GCCTCCATCTCTTGCAGATCTAGTCAGAGCATTGTACATAGTAATGGAAACACCT
ATTTAGAATGGTACCTGCAGAAACCAGGCCAGTCTCCAGAGCTCCTGATCTACA
AAGTTTACAACCGATTTTCTGGGGTCCCAGACAGGTTCAGTGGCAGTGGATCA
GGGACAGATTTCACACTCAAGATCAGCAGAGTGGAGGCTGAGGATCTGGGAGT
TTATTACTGCTTTCAAGGTTCACATGTTCCATTCACGTTCGGCTCGGGGACAAA
GTTGGAAATAAAA Heavy chain (SEQ ID NO. 21)
<------------FR1-------------> CDR1 <----FR2---->        CDR2
QVQLQQSGAELVRPGASVTLSCKASGYTFTDYEMHWVKQTPVHGLEWIGAIDPETGGAAYNQKFKG
<-------------FR3--------------->        CDR3      <---FR4--->
KAILTADKSSSTAYMELRSLTSEDSAVYYCTREGITTSVVTYYWYFDVWGTGTTVTSS Nucleic acid sequence (SEQ ID NO. 27)
CAGGTTCAACTGCAGCAGTCTGGGGCTGAGCTGGTGAGGCCTGGGGCTTCAGT
GACGCTGTCCTGCAAGGCTTCGGGCTACACATTTACTGACTATGAAATGCACTG
GGTGAAGCAGACACCTGTGCATGGCCTGGAATGGATtGGAGCTATTGATCCTGA
AACTGGTGGTGCTGCCTACAATCAGAAGTTCAAGGGCAAGGCCATACTGACTG
CAGACAAATCCTCCAGCACAGCCTACATGGAGCTCCGCAGCCTGACATCTGAG
GACTCTGCCGTCTATTACTGTACAAGAGAGGGTATTACTACGTCAGTGGTTACGT
ACTACTGGTACTTCGATGTCTGGGGCACAGGGACCACGGTCACCGTCTCCTCA Light chain (SEQ ID NO. 22)
<--------FR1--------->        CDR1        <-----FR2---->    CDR2
DVLMTQTPLSLPVSLGDQASISCRSSQSIVHSNGNTYLEWLQKPGQSPKLLIYKVSNRFS
<-------------FR3--------------->        CDR2      <--FR4-->
GVPDRFSGSGSGTDFTLRISRVEPEDLGVYYCFQGSHVPLTFGSGTKLEIK Nucleic acid sequence (SEQ ID NO. 28)
GATGTTTTGATGACCCAAACTCCACTCTCCCTGCCTGTCAGTCTTGGAGATCAA
GCCTCCATCTCTTGCAGATCTAGTCAGAGCATTGTACATAGTAATGGAAACACCT
ATTTAGAATGGTACCTGCAGAAACCAGGCCAGTCTCCAAAGCTCCTGATCTACA
AAGTTTCCAACCGATTTTCTGGGGTCCCAGACAGGTTCAGTGGCAGTGGATCA
GGGACAGATTTCACACTCAGGATCAGCAGAGTGGAGCCTGAGGATCTGGGAGT
TTATTACTGCTTTCAAGGTTCACATGTTCCACTCACGTTCGGCTCGGGGACAAA
GTTGGAAATAAAA Clone 11:
Heavy chain (SEQ ID NO. 23)
<------------FR1-------------> CDR1 <----FR2---->        CDR2
QVTLKESGPGILQPSQTLSLTCSFSGFSLSTFGMGVGWIRQPSGKGLEWLAHIWWDDDKYYNPALKS
<-------------FR3--------------->        CDR2      <---FR4--->
RLTISKNTSKNQVFLKIANVDTEDTATYYCARIEERFRWYFDVWGTGTTVTSS Nucleic acid sequence (SEQ ID NO. 29)
CAGGTTACTCTGAAAGAGTCTGGCCCTGGGATATTGCAGCCCTCCCAGACCCTC
AGTCTGACTTGTTCTTTCTCTGGGTTTTCACTGAGCACTTTTGGTATGGGTGTCG
GCTGGATTCGTCAGCCTTCAGGGAAGGGTCTGGAGTGGCTGGCACACATTTGG
TGGGATGATGATAAGTACTATAATCCCGCCCTGAAGAGTCGGCTCACAATCTCC
AAGAATACCTCCAAAAACCAGGTATTCCTCAAGATCGCCAATGTGGACACTGA
AGATACTGCCACATACTACTGTGCTCGAATAGAGGAGAGGTTCCGCTGGTACTT
CGATGTCTGGGGCACAGGGACCACGGTCACCGTCTCCTCA Light chain (SEQ ID NO. 24)
<--------FR1--------->        CDR1        <-----FR2---->    CDR2
RAGWTQESALTTSPGETVTLTCRSSTGAITTSNYANWVQKPDHLFTGLIGGTNNRAP
<-------------FR3--------------->        CDR2      <--FR4-->
GVPARFSGSLIGDKAALTITGAQTEDEAIYFCALWYSNHWVFGGGTKLTVL
```

-continued

```
Nucleic acid sequence (SEQ ID NO. 30)
AGGGCTGGTTGGACTCAGGAATCTGCACTCACCACATCACCTGGTGAAACAGT
CACACTCACTTGTCGCTCAAGTACTGGGGCTATTACAACTAGTAACTATGCCAA
CTGGGTCCAAGAAAAACCAGATCATTTATTCACTGGTCTAATAGGTGGTACCAA
CAACCGAGCTCCAGGTGTTCCTGCCAGATTCTCAGGCTCCCTGATTGGAGACA
AGGCTGCCCTCACCATCACAGGGGCACAGACTGAGGATGAGGCAATATATTTCT
GTGCTCTATGGTACAGCAACCACTGGGTGTTCGOTGGAGGAACCAAACTGACT
GTCCTA
```

Example 7

Construct the Expression Vector of Chimeric Antibody

The Fc fragment of the constant region of the heavy chain and the κ/λ constant region of the light chain from human blood cells (Beijing Blood Institute) were cloned into the plasmid pCDNA3.1 (see Walls Mass., Hsiao H and Harris L J (1993), Nucleic Acids Research, Vol. 21, No. 12 2921 -2929) for modification. Said sequence fragments of the heavy chain and light chain described in Example 6 were synthesized by Genscript Corporation. The heavy chain sequence fragment, after digestion by Xho I and Age I enzymes, and the light chain sequence fragment, after digestion by Sma I and Dra III enzymes, were cloned into the plasmid pCDNA3.1 and sequenced to confirm the sequence of cloned DNA. The experimental materials in the description below were all obtained through transfecting the cells with this series of plasmids and purifying the products generated by the transfected cells.

Example 8

Figure 5:
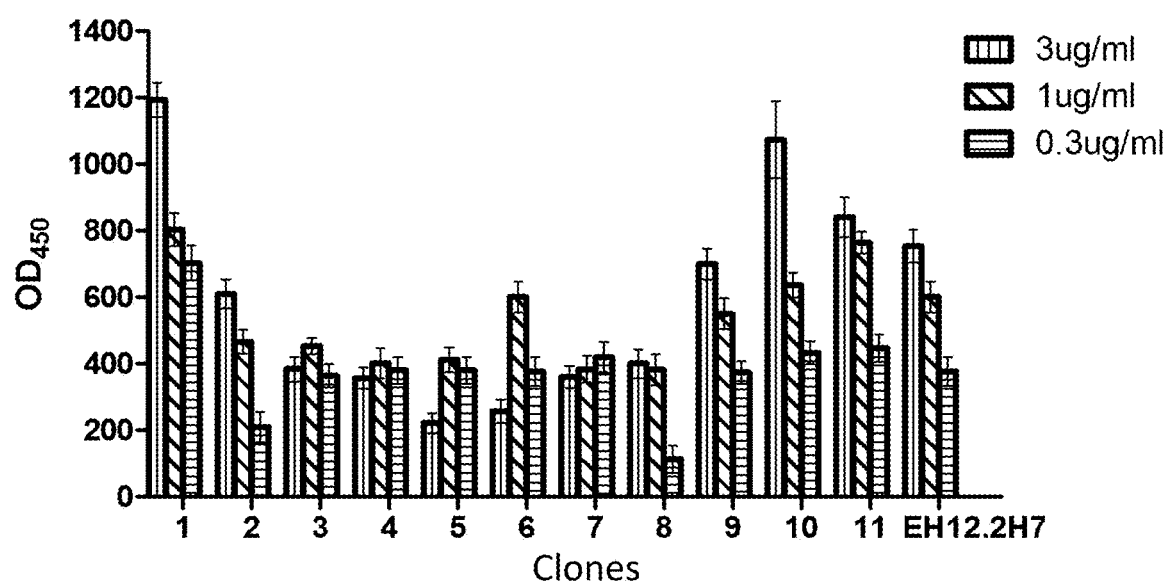
FIG. 5 shows the results of the tetanus toxin stimulation experiments measuring the in vitro stimulation of chimeric antibody on T cells.

In Vitro Stimulation of T Cells by Chimeric Antibody—Tetanus Toxin Stimulation Test Freshly prepared peripheral blood mononuclear cell (PBMC) were placed into 96-well flat-bottom plate. After an overnight incubation, various concentrations of antibodies and 100 ng/ml of tetanus toxin (TT) (List Biological Laboratories) were added. Supernatant was collected from each of the sample well three days later,. The content of IFNγ in the supernatant was measured by ELISA using the INFNγ kit (R&D System). As shown in FIG. 5, after the PD-1 signal is blocked, the cytokine secretion by the immune cells activated by the TT stimulation increased significantly. In addition, the titers of the candidate antibodies are higher than EH12.2H7, an antibody described in the Chinese patent application CN 200980147059.0 and purchased from Biolegend Corporation.

Example 9

Interaction of various antibodies with PD-1 after exchange of heavy and light chains of the former Using the method described in Example 7, the light and heavy chains of the antibodies 1 and 10 were recombined reciprocally to generate recombinant antibodies H1L10 (heavy chain 1, light chain 10) and H10L1 (heavy chain 10, light chain 1). These antibodies, the original antibody 1 (heavy chain 1, light chain 1) and the original antibody 10 (heavy chain 10, light chain 10) were tested by ELISAs and the results of EC50s for these antibodies are shown in the table below:

| Sample | H1L1 | H10L10 | H1L10 | H10L1 |
|---|---|---|---|---|
| EC50 (pM) | 338.1 | 426.3 | 270.1 | 528.1 |

The result shows that the antibodies produced after recombination can still bind to PD-1 protein effectively.

Example 10

Humanization Modification of Antibody

The humanization modification was conducted based on the sequence of variable region of the antibody secreted by the hybridoma cell obtained as described above. In brief, the process of humanization modification involved the following steps: A—comparing the gene sequences of the antibodies secreted by various hybridoma cells with the gene sequence of the human embryonic antibody to find the sequence of high homology; B—analyzing and testing the affinity of HLA-DR in order to select the framework sequence of human embryo with low affinity; C—using computer analog technology to apply molecular docking to analyze the sequences of framework amino acids in the variable region and the surrounding, and examining its spatial stereo binding mode; calculating the electrostatic force, Van der Waals force, hydrophobicity-hydrophilicity and the entropy value to analyze the key individual amino acids in the gene sequences of the antibodies secreted by various hybridoma cell, which are critical for interacting with PD-1 and maintaining the antibodies' spatial configuration, grafting these key amino acids back to the selected gene framework of human embryo. The amino acid sites in the framework region which must be reserved were also identified and random primers were synthesized to construct the phage library. The humanized antibody library was then screened (Pini, A.et al., (1998). Design and Use of a Phage Display Library: HUMAN ANTIBODIES WITH SUB-NANOMOLAR AFFINITY AGAINST A MARKER OF ANGIOGENESIS ELUTED FROM A TWO-DIMENSIONAL GEL., Journal of Biological Chemistry, 273(34): 21769-21776). A number of humanized antibodies were obtained from the screening, including the following clones. The light chain sequences of Clone 38, 39 and 41 are the same, and the heavy chain sequences of Clone 39 and 48 are the same.

Heavy chain of Clone 38 (SEQ ID NO. 33 (peptide); SEQ ID NO. 38 (nucleotide))
<------------FR1-------------> CDR1 <----FR2----> CDR2
QGQLVQSGAEVKKPGASVKVSCKASGYTFTDYEMHWVRQAPIHGLEWIGVIESETGGTAYNQKFKG
<-------------FR3--------------> CDR3 <---FR4--->
RVTITADKSTSTAYMELSSLRSEDTAVYYCAREGITTVATTYYWYFDVWGQGTTVTSS
CAGGGCCAGCTGGTGCAGAGCGGCGCCGAGGTGAAGAAGCCCGGCGCCAGCG
TGAAGGTGAGCTGCAAGGCCAGCGGCTACACCTTCACCGACTACGAGATGCAC
TGGGTGAGACAGGCCCCCATCCACGGCCTGGAGTGGATCGGCGTGATCGAGAG
CGAGACCGGCGGCACCGCCTACAACCAGAAGTTCAAGGGCAGAGTGACCATC
ACCGCCGACAAGAGCACCAGCACCGCCTACATGGAGCTGAGCAGCCTGAGAA
GCGAGGACACCGCCGTGTACTACTGCGCCAGAGAGGGCATCACCACCGTGGCC
ACCACCTACTACTGGTACTTCGACGTGTGGGGCCAGGGCACCACCGTGACCGT
GAGCAGC Light chain of Clone 38 (SEQ ID NO. 34 (peptide); SEQ ID NO. 30 (nucleotide))
<--------FR1---------> CDR1 <------FR2----> CDR2
DVVMTQSPLSLPVTLGQPASISCRSSQSIVHSNGNTYLEWYLQKPGQSPQLLIYKVSNRFS
<--------------FR3---------------> CDR3 <--FR4-->
GVPDRFSGSGSGTDFTLKISRVEAEDLGVYYCFQGSHVPFTFGQGTKLEIK
GATGTGGTGATGACCCAGAGCCCGCTGAGCCTGCCGGTGACCCTGGGCCAGCC
GGCGAGCATTAGCTGCCGCAGCAGCCAGAGCATTGTGCATAGCAACGGCAACA
CCTATCTGGAATGGTATCTGCAGAAACCGGGCCAGAGCCCGCAGCTGCTGATTT
ATAAAGTGAGCAACCGCTTTAGCGGCGTGCCGGATCGCTTTAGCGGCAGCGGC
AGCGGCACCGATTTTACCCTGAAAATTAGCCGCGTGGAAGCGGAAGATGTGGG
CGTGTATTATTGCTTTCAGGGCAGCCATGTGCCGCTGACCTTTGGCCAGGGCAC
CAAACTGGAAATTAAA Heavy chain of Clone 39 (SEQ ID NO. 39 (peptide); SEQ ID NO. 40 (nucleotide))
<------------FR1-------------> CDR1 <----FR2----> CDR2
QGQLVQSGAEVKKPGASVKVSCKASGYTFTDYEMHWVRQAPGQGLEWMGVIESETGGTAYNQKFKG
<-------------FR3--------------> CDR3 <---FR4--->
RAKITADKSTSTAYMELSSLRSEDTAVYYCTREGITTVATTYYWYFDVWGQGTTVTSS
CAGGGCCAGCTGGTGCAGAGCGGCGCCGAGGTGAAGAAGCCCGGCGCCAGCG
TGAAGGTGAGCTGCAAGGCCAGCGGCTACACCTTCACCGACTACGAGATGCAC
TGGGTGAGACAGGCCCCCGGCCAGGGCCTGGAGTGGATGGGCGTGATCGAGA
GCGAGACCGGCGGCACCGCCTACAACCAGAAGTTCAAGGGCAGAGCCAAGAT
CACCGCCGACAAGAGCACCAGCACCGCCTACATGGAGCTGAGCAGCCTGAGA
AGCGAGGACACCGCCGTGTACTACTGCACCAGAGAGGGCATCACCACCGTGGC
CACCACCTACTACTGGTACTTCGACGTGTGGGGCCAGGGCACCACCGTGACCG
TGAGCAGC Light chain of Clone 39 (SEQ ID NO. 34 (peptide); SEQ ID NO. 30))
<--------FR1---------> CDR1 <------FR2----> CDR2
DVVMTQSPLSLPVTLGQPASISCRSSQSIVHSNGNTYLEWLQKPGQSPQLLIYKVSNRFS
<--------------FR3---------------> CDR3 <--FR4-->
GVPDRFSGSGSGTDFTLKISRVEAEDVGVYYCFQGSHVPLTFGQGTKLEIK
GATGTGGTGATGACCCAGAGCCCGCTGAGCCTGCCGGTGACCCTGGGCCAGCC
GGCGAGCATTAGCTGCCGCAGCAGCCAGAGCATTGTGCATAGCAACGGCAACA
CCTATCTGGAATGGTATCTGCAGAAACCGGGCCAGAGCCCGCAGCTGCTGATTT
ATAAAGTGAGCAACCGCTTTAGCGGCGTGCCGGATCGCTTTAGCGGCAGCGGC
AGCGGCACCGATTTTACCCTGAAAATTAGCCGCGTGGAAGCGGAAGATGTGGG
CGTGTATTATTGCTTTCAGGGCAGCCATGTGCCGCTGACCTTTGGCCAGGGCAC
CAAACTGGAAATTAAA Heavy chain of Clone 41 (SEQ ID NO. 36 (peptide); SEQ ID NO. 41 (nucleotide))
<------------FR1-------------> CDR1 <----FR2----> CDR2
QGQLVQSGAEVKKPGASVKVSCKASGYTFTDYEMHWVRQAPGQGLEWMGVIESETGGTAYNQKFQG
<-------------FR3--------------> CDR3 <---FR4--->
RVTLTADKSSSTAYMELSSLRSEDTVYYCTREGITTVATTYYWYFDVWGQGTLVTVSS
CAGGGCCAGCTGGTGCAGAGCGGCGCGGAAGTGAAAAAACCGGGCGCGAGC
GTGAAAGTGAGCTGCAAAGCGAGCGGCTATACCTTTACCGATTATGAAATGCAT
TGGGTGCGCCAGGCGCCGGGCCAGGGCCTGGAATGGATGGGCGTGATTGAAA
GCGAAACCGGCGGCACCGCGTATAACCAGAAATTTCAGGGCCGCGTGACCCTG
ACCGCGGATAAAAGCAGCAGCACCGCGTATATGGAACTGAGCAGCCTGCGCAG
CGAAGATACCGCGGTGTATTATTGCACCCGCGAAGGCATTACCACCGTGGCGAC
CACCTATTATTGGTATTTTGATGTGTGGGGCCAGGGCACCCTGGTGACCGTGAG
CAGC Light chain of Clone 41 (SEQ ID NO. 34 (peptide); SEQ ID NO. 30 (nucleotide))
<--------FR1---------> CDR1 <------FR2----> CDR2
DVVMTQSPLSLPVTLGQPASISCRSSQSIVHSNGNTYLEWYLQKPGQSPQLLIYKVSNRFS
<--------------FR3---------------> CDR3 <--FR4-->
GVPDRFSGSGSGTDFTLKISRVEAEDVGVYYCFQGSHVPLTFGQGTKLEIK
GATGTGGTGATGACCCAGAGCCCGCTGAGCCTGCCGGTGACCCTGGGCCAGCC
GGCGAGCATTAGCTGCCGCAGCAGCCAGAGCATTGTGCATAGCAACGGCAACA
CCTATCTGGAATGGTATCTGCAGAAACCGGGCCAGAGCCCGCAGCTGCTGATTT
ATAAAGTGAGCAACCGCTTTAGCGGCGTGCCGGATCGCTTTAGCGGCAGCGGC
AGCGGCACCGATTTTACCCTGAAAATTAGCCGCGTGGAAGCGGAAGATGTGGG
CGTGTATTATTGCTTTCAGGGCAGCCATGTGCCGCTGACCTTTGGCCAGGGCAC
CAAACTGGAAATTAAA

```
Heavy chain of Clone 48 (SEQ ID NO. 35 (peptide); SEQ ID NO. 40 (nucleotide))
<------------FR1-------------> CDR1 <----FR2----->       CDR2
QGQLVQSGAEVKKPGASVKVSCKASGYTFTDYEMHWVRQAPGQGLEWMGVIESETGGTAYNQKFQG
<--------------FR3--------------->    CDR3          <---FR4--->
RAKITADKSTSTAYMELSSLRSEDTAVYYCTREGITTVATTYYWYFDVWGQGTLVTVSS
CAGGGCCAGCTGGTGCAGAGCGGCGCCGAGGTGAAGAAGCCCGGCGCCAGCG
TGAAGGTGAGCTGCAAGGCCAGCGGCTACACCTTCACCGACTACGAGATGCAC
TGGGTGAGACAGGCCCCCGGCCAGGGCCTGGAGTGGATGGGCGTGATCGAGA
GCGAGACCGGCGGCACCGCCTACAACCAGAAGTTCAAGGGCAGAGCCAAGAT
CACCGCCGACAAGAGCACCAGCACCGCCTACATGGAGCTGAGCAGCCTGAGA
AGCGAGGACACCGCCGTGTACTACTGCACCAGAGAGGGCATCACCACCGTGGC
CACCACCTACTACTGGTACTTCGACGTGTGGGGCCAGGGCACCACCGTGACCG
TGAGCAGC Light chain of Clone 48 (SEQ ID NO. 37 (peptide); SEQ ID NO. 42 (nucleotide))
<---------FR1---------->         CDR1        <------FR2---->  CDR2
DVVMTQSPLSLPVTLGQPASISCRSSQSIVHSNGNTYLEWYLQKPGQSPQLLIYKVSNRFS
<--------------FR3-------------->    CDR3---S--FR4-->
GVPDRFSGSGSGTDFTLKISRVEAEDVGVYYCFQGSHVPLTFGQGTKLEIK
GA
TGTGGTGATGACCCAGAGCCCGCTGAGCCTGCCGGTGACCCTGGGCCAGCCGG
CGAGCATTAGCTGCCGCAGCAGCCAGAGCATTGTGCATAGCAACGGCAACACC
TATCTGGAATGGTATCTGCAGAAACCGGGCCAGAGCCCGCGCCTGCTGATTTAT
AAAGTGAGCAACCGCTTTAGCGGCGTGCCGGATCGCTTTAGCGGCAGCGGCAG
CGGCACCGATTTTACCCTGAAAATTAGCCGCGTGGAAGCGGAAGATGTGGGCG
TGTATTATTGCTTTCAGGGCAGCCATGTGCCGCTGACCTTTGGCCAGGGCACCA
AACTGGAAATTAAA
```

Example 11

In Vitro Stimulation of T Cells by Humanized Antibody

Figure 6:
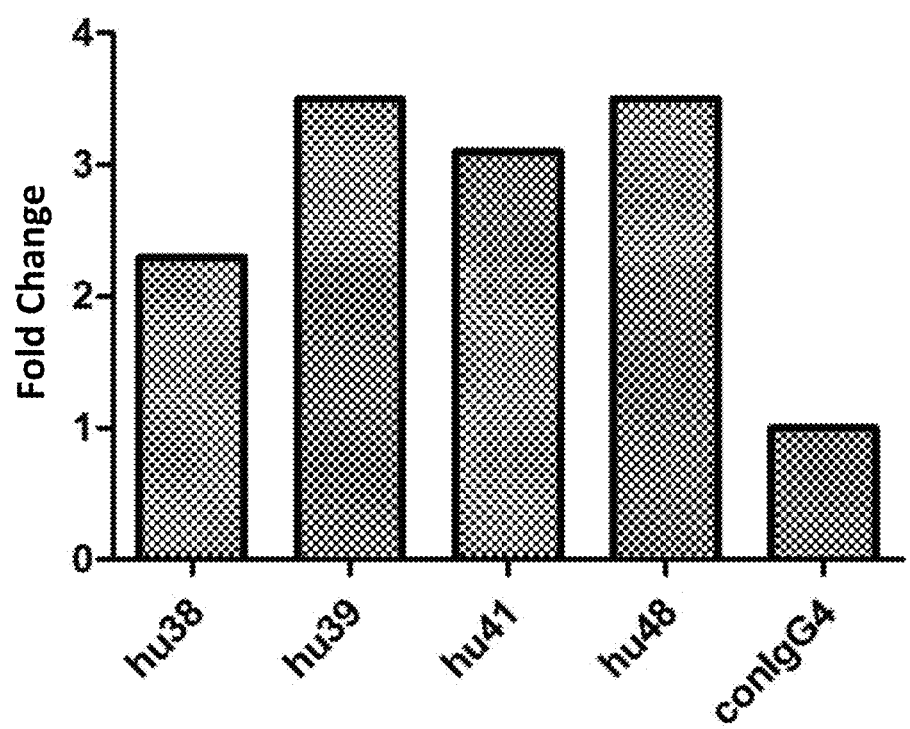
FIG. 6 shows the secretion levels of IL2 by Clones hu38 ("38"), hu39 ("39"), hu41 ("41") and hu48 ("48") (control (conIgG4)) of the humanized antibody measured by the CD8+ cytokine assay kit.

Freshly prepared PBMCs (Beijing Blood Institute) were placed in the wells of a 96-well flat-bottom plate. After an overnight incubation, 10 ug/ml of antibody and 100 ng/ml of tetanus toxin (TT) were added to the PBMCs. After culturing it for 3 days, the supernatant was collected and the secretion level of IL2 of Clones 38, 39, 41, 48, and conIgG4 (control antibody) of the humanized antibodies were measured using Luminex° (Thermo Fisher Scientific, Inc.) and CD8+ cytokine assay detection kit (EMD Millipore, Inc.). The result (see FIG. 6) shows that all the humanized antibodies can stimulate the T cells.

Example 12

Humanized Antibody can Stimulate T Cells to Kill Tumor Cells in Vitro

Figure 7:
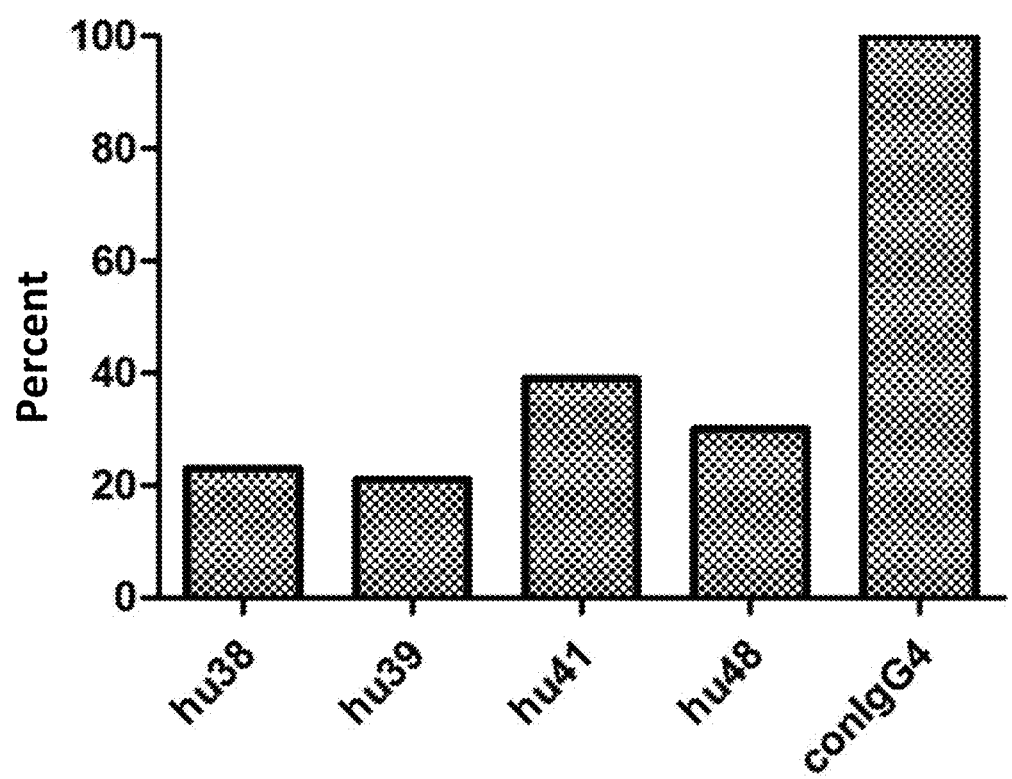
FIG. 7 shows the values of the GFP fluorescence of Clones 38, 39, and 41 relative to Clone 48 (control IgG4) of the humanized anti-PD-1 antibody in experiments where dendritic cells and the modified MD-MAB-453 cells were cultured together for 3 days followed by the addition of extracted T cells and each of the Clones to culture together for an additional 3 days.

MD-MAB-453 cells were infected with the lentivirus (Qiagen) expressing PD-L1 protein to generate a MD-MAB-453 cell line, which stably expresses PD-L1. A GFP gene was also introduced to said cell line to allow the stable expression of the GFP protein. Dendritic cells (DC) isolated from the fresh human peripheral blood cells 300 cells/well were cultured with said MD-MAB-453 cells stably expressing both PD-L1 and GFP (300 cells/well) in a 96-well plate together for three days. T cells (1000 cells/well) isolated from human peripheral blood and 10 ug/ml of the humanized anti-PD-1 antibody Clones 38, 39, 41, 48 or the control antibody "conIgG4" were added to the mixture and cultured together for 3 days to before the GFP fluorescence was measured. The result (see FIG. 7) shows that all the humanized antibodies can stimulate T cells to kill the tumor cells.

Example 13

Figure 8A:
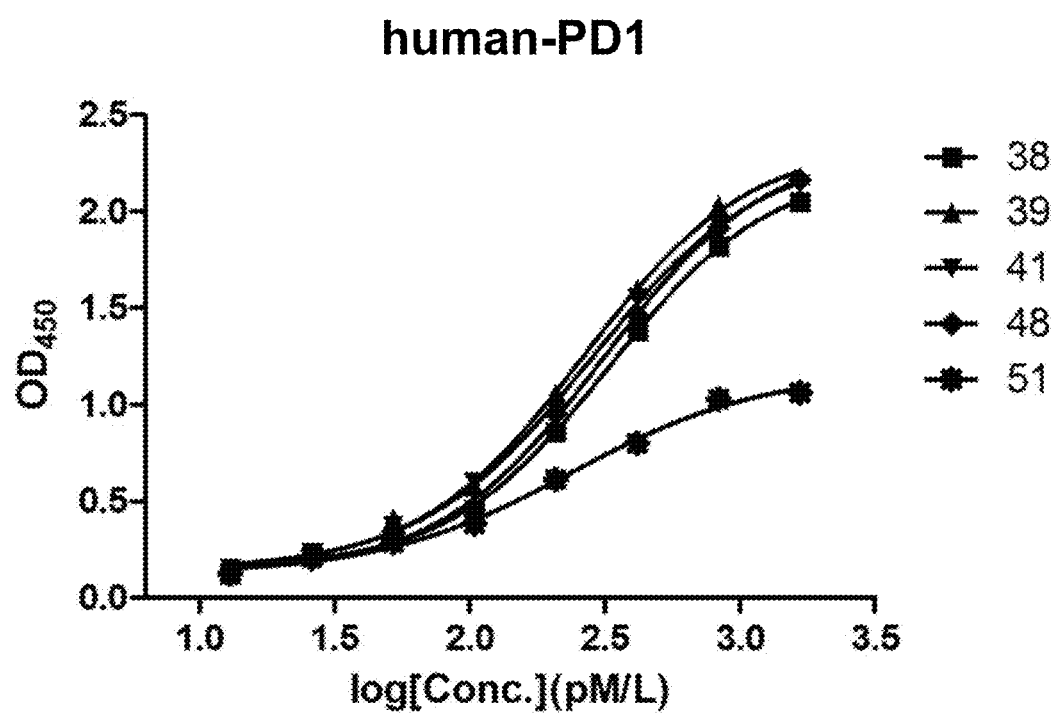
FIGS. 8A-8C show the binding between the humanized antibody according to the present invention with the PD-1 proteins derived from human (FIG. 8A), *Macaca fascicularis* (FIG. 8B), and mouse (FIG. 8C).
Figure 8B:
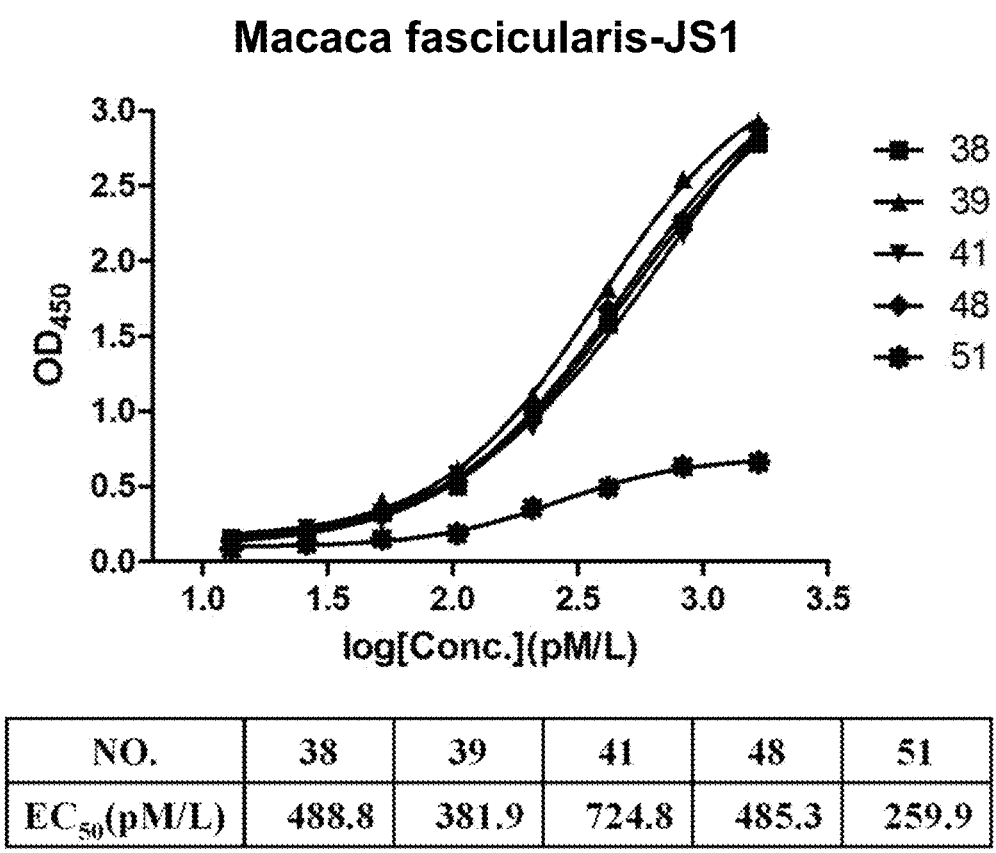
Figure 8C:
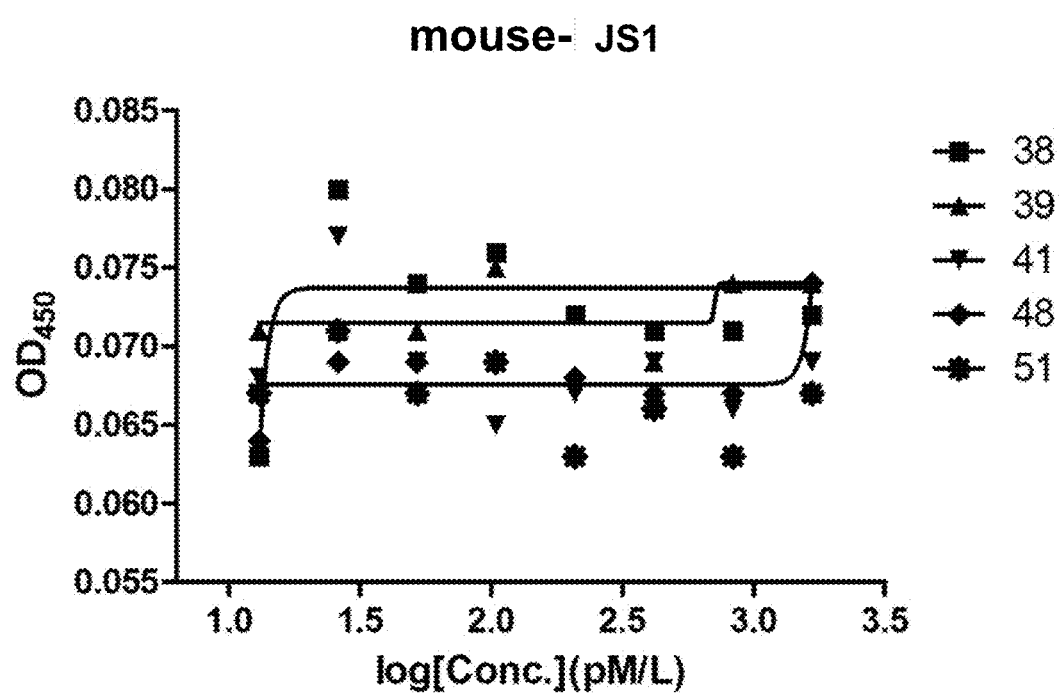

The Binding of Humanized Antibodies with PD-1 Proteins Derived from Various Species 1 ug/ml of human-derived PD-1, *Macaca fascicularis* PD-1, and mouse-derived PD-1 (Sinobiological) in the carbonate buffer solution (0.05 M PH9) were prepared and used to coat the wells of the 96-well flat-bottom plates at 4° C. overnight. The next day, solution was removed from the wells and the wells were washed three times with a washing buffer. PBS solution containing 3% BSA was added to block the wells for 20 minutes. The wells were then washed three times with the washing buffer before 100 ul of various concentrations of candidate antibodies were added. The mixture was incubated at room temperature for 1 hour and then washed three times with a washing buffer. A HRP conjugated goat anti human antibody (Jackson Immunoresearch) was first diluted to 1:10000 with the washing buffer and then added to the wells to incubate at room temperature for 1 hour. After washing three times with the washing buffer, 50 ul TMB substrate solution was added to the wells to develop the color. After 10 minutes at room temperature, the color development reaction was terminated with 25 ul 0.5M sulfuric acid solution and the absorbance was read at 450 nm. The results (FIG. 8A, B and C) show that all clones bind to PD-1 of human or *Macaca fascicularis* with similar affinity, but not with the mouse-derived PD-1.

Compare PD-1 sequences of human, *Macaca fascicularis* and mouse (see FIG. 9 in which the main different regions of mouse PD-1 and PD-1 of human/*Macaca fascicularis* are boxed). Experimental results have proved that the epitope of the candidate antibody that binds to PD-1 protein exists in these regions.

Example 14

Figure 10:
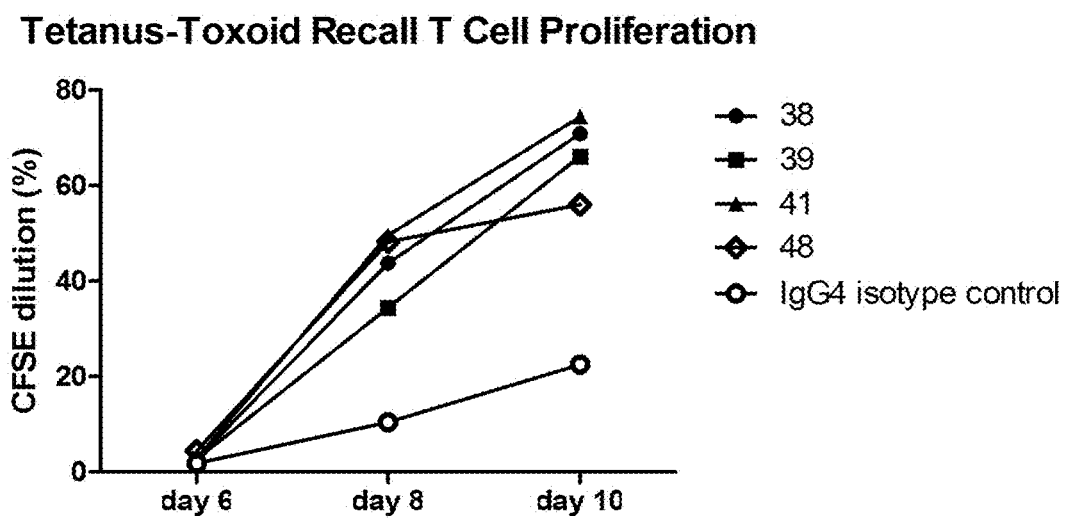
FIG. 10 shows the experiment result of T cell proliferation in vitro stimulated by humanized antibody—tetanus antigen memory response.

Experiment of in Vitro Stimulation by Humanized Antibody to T Cell Proliferation—Tetanus Antigen Memory Response Experiment Freshly prepared PBMC (Beijing Blood Institute) were placed into the wells of a 96-well flat-bottom plate. After incubation overnight, the cells were labeled with carboxyfluorescein succinimidyl ester (CFSE) and incubated with 10 ug/ml of humanized antibody (38, 39, 41 and 48) and 100 ng/ml of tetanus toxin (TT) (List Biological Laboratories). T cell proliferation at the $6^{th}$, $8^{th}$ and $10^{th}$ day was analyzed based on the dilution ratio of CSFE with the flow cytometry (FACS). As shown by the result of FIG. 10, compared with the control IgG the immune cells activated by TT stimulation induced through blocking the PD-1 signal was under further division and proliferation.

Example 15

Figure 11:
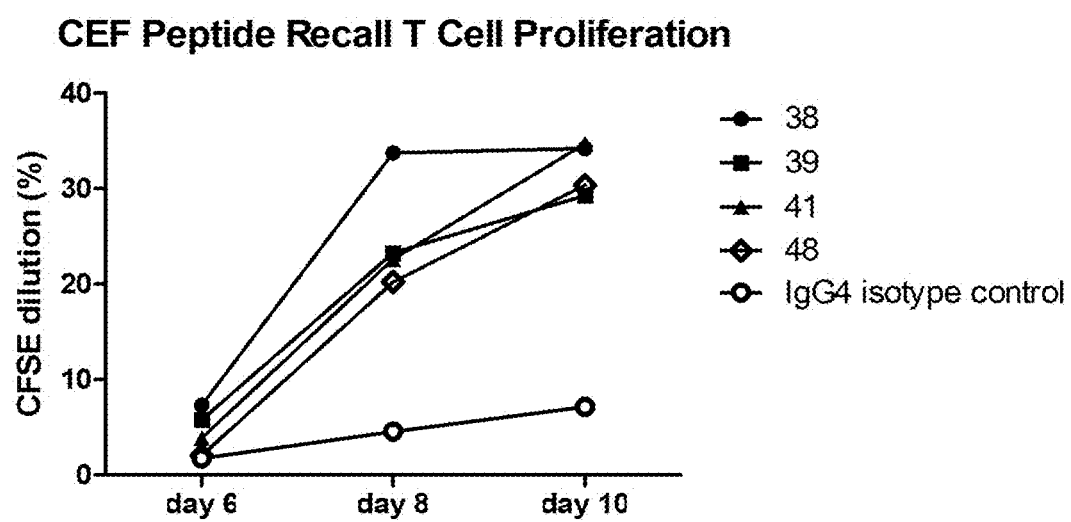
FIG. 11 shows the experiment result of T cell proliferation in vitro stimulated by humanized antibody—viral polypeptides antigen memory response.

In Vitro Stimulation of T Cell Proliferation by Humanized Antibody—Viral Polypeptides Antigen Memory Response Experiment Freshly prepared PBMCs (Beijing Blood Institute) were placed into the wells of a 96-well flat-bottom plate. After an overnight incubation, the cells were labeled with CFSE. 10 ug/ ml of humanized antibody (38, 39, 41 and 48) and 1 ug/ml of peptide mixture of CMV, EBV and Influenza ("CEF") were added to the wells. Quantitative analysis were conducted on T cell proliferation at the $6^{th}$, $8^{th}$ and $10^{th}$ day with the flow cytometry (FACS) based on the dilution ratio of CSFE. As shown by the result of FIG. 11, compared with the control IgG the immune cells activated by CEF mixed polypeptides stimulation induced through blocking the PD-1 signal was under further division and proliferation.

---

What is claimed is:

1. An antibody or a functional fragment thereof that can bind to the programmed cell death 1 (PD-1) protein having an amino acid sequence of SEQ ID NO: 43, wherein the antibody or a functional fragment thereof comprises:
    i) a heavy chain CDR1 having the amino acid sequence of Asp Tyr Glu Met His (SEQ ID NO: 1),
    ii) a heavy chain CDR2 having the amino acid sequence of Val Ile Glu Ser Glu Thr Gly Gly Thr Ala Tyr Asn Gln Lys Phe Lys Gly (SEQ ID NO: 2),
    iii) a heavy chain CDR3 having the amino acid sequence of Glu Gly Ile Thr Thr Val Ala Thr Thr Tyr Tyr Trp Tyr Phe Asp Val (SEQ ID NO: 3),
    iv) a light chain CDR1 having the amino acid sequence of Arg Ser Ser Gln Ser Ile Val His Ser Asn Gly Asn Thr Tyr Leu Glu (SEQ ID NO: 10),
    v) a light chain CDR2 having the amino acid sequence of Lys Val Ser Asn Arg Phe Ser (SEQ ID NO: 11), and
    vi) a light chain CDR3 having the amino acid sequence of Phe Gln Gly Ser His Val Pro Leu Thr (SEQ ID NO: 12).

2. The antibody or functional fragment thereof according to claim 1, which comprises a heavy chain variable region having the amino acid sequence of SEQ ID NO: 19, or an amino acid sequence having at least 95% sequence identity with SEQ ID NO: 19, and/or a light chain variable region having the amino acid sequence of SEQ ID NO: 22, or an amino acid sequence having at least 95% sequence identity with SEQ ID NO: 22.

3. The antibody or functional fragment thereof according to claim 1, wherein the antibody or functional fragment thereof is a chimeric antibody or a humanized antibody.

4. The antibody or functional fragment according to claim 1 comprising a heavy chain variable region comprising the amino acid sequence of SEQ ID NO: 35 or an amino acid sequence that has at least 95% sequence identity with SEQ ID NO: 35, and/or a light chain variable region comprising the amino acid sequence of SEQ ID NO: 37 or an amino acid sequence that has at least 95% sequence identity with SEQ ID NO: 37.

5. The antibody or functional fragment according to claim 1, comprising a heavy chain variable region comprising SEQ ID NO: 35 or an amino acid sequence that has at least 95% sequence identity with SEQ ID NO: 35 and a light chain variable region comprising SEQ ID NO: 37 or an amino acid sequence that has at least 95% sequence identity with SEQ ID NO: 37.

6. A isolated nucleic acid molecule, which encodes said antibody or functional fragment thereof of claim 1.

7. An expression vector, which comprises said nucleic acid molecule of claim 6.

8. A host cell, which comprises said expression vector of claim 7.

9. A method of producing the anti-PD-1 antibody or a functional fragment thereof of claim 1, wherein the method comprises: culturing a host cell of claim 8 under conditions that allow production of said antibody or functional fragment thereof, and recovering said antibody or functional fragment thereof so produced.

10. An immunoconjugate, comprising said antibody or functional fragment thereof of claim 1 that is coupled with a therapeutic agent, wherein said therapeutic agent is a toxin, radioisotope, drug, or cytotoxic agent.

11. A pharmaceutical composition comprising the antibody or functional fragment thereof of claim 1 and a pharmaceutical carrier.

* * * * *

```
                        SEQUENCE LISTING

<160> NUMBER OF SEQ ID NOS: 45

<210> SEQ ID NO 1
<211> LENGTH: 5
<212> TYPE: PRT
<213> ORGANISM: Artificial Sequence
<220> FEATURE:
<223> OTHER INFORMATION: synthetic heavy chain CDR1 of clone 1

<400> SEQUENCE: 1

Asp Tyr Glu Met His
1               5

<210> SEQ ID NO 2
<211> LENGTH: 17
<212> TYPE: PRT
<213> ORGANISM: Artificial Sequence
<220> FEATURE:
<223> OTHER INFORMATION: synthetic heavy chain CDR2 of clone 1

<400> SEQUENCE: 2

Val Ile Glu Ser Glu Thr Gly Gly Thr Ala Tyr Asn Gln Lys Phe Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: synthetic heavy chain CDR3 of clone 1

<400> SEQUENCE: 3

Glu Gly Ile Thr Thr Val Ala Thr Thr Tyr Tyr Trp Tyr Phe Asp Val
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: synthetic light chain CDR1 of clone 1

<400> SEQUENCE: 4

Arg Ser Ser Gln Ser Ile Val His Ser Asn Gly Asn Thr Tyr Leu Glu
1               5                   10                  15
```

```
<210> SEQ ID NO 5
<211> LENGTH: 7
<212> TYPE: PRT
<213> ORGANISM: Artificial Sequence
<220> FEATURE:
<223> OTHER INFORMATION: synthetic light chain CDR2 of clone 1

<400> SEQUENCE: 5

Lys Val Tyr Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic light chain CDR3 of clone 1

<400> SEQUENCE: 6

Phe Gln Gly Ser His Val Pro Phe Thr
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic heavy chain CDR1 of clone 10

<400> SEQUENCE: 7

Asp Tyr Glu Met His
1               5

<210> SEQ ID NO 8
<211> LENGTH: 16
<212> TYPE: PRT
<213> ORGANISM: Artificial Sequence
<220> FEATURE:
<223> OTHER INFORMATION: synthetic heavy chain CDR2 of clone 10

<400> SEQUENCE: 8

Ala Ile Asp Pro Glu Thr Gly Gly Ala Ala Tyr Asn Gln Lys Phe Lys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: synthetic heavy chain CDR3 of clone 10

<400> SEQUENCE: 9

Glu Gly Ile Thr Thr Ser Val Val Thr Tyr Tyr Trp Tyr Phe Asp Val
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: synthetic light chain CDR1 of clone 10

<400> SEQUENCE: 10

Arg Ser Ser Gln Ser Ile Val His Ser Asn Gly Asn Thr Tyr Leu Glu
1               5                   10                  15
```

```
<210> SEQ ID NO 11
<211> LENGTH: 7
<212> TYPE: PRT
<213> ORGANISM: Artificial Sequence
<220> FEATURE:
<223> OTHER INFORMATION: synthetic light chain CDR2 of clone 10

<400> SEQUENCE: 11

Lys Val Ser Asn Arg Phe Ser
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic light chain CDR3 of clone 10

<400> SEQUENCE: 12

Phe Gln Gly Ser His Val Pro Leu Thr
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic heavy chain CDR1 of clone 11

<400> SEQUENCE: 13

Thr Phe Gly Met Gly Val Gly
1               5

<210> SEQ ID NO 14
<211> LENGTH: 16
<212> TYPE: PRT
<213> ORGANISM: Artificial Sequence
<220> FEATURE:
<223> OTHER INFORMATION: synthetic heavy chain CDR2 of clone 11

<400> SEQUENCE: 14

His Ile Trp Trp Asp Asp Asp Lys Tyr Tyr Asn Pro Ala Leu Lys Ser
1               5                   10                  15

<210> SEQ ID NO 15
<211> LENGTH: 11
<212> TYPE: PRT
<213> ORGANISM: Artificial Sequence
<220> FEATURE:
<223> OTHER INFORMATION: synthetic heavy chain CDR3 of clone 11

<400> SEQUENCE: 15

Ile Glu Glu Arg Phe Arg Trp Tyr Phe Asp Val
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthetic light chain CDR1 of clone 11

<400> SEQUENCE: 16

Arg Ser Ser Thr Gly Ala Ile Thr Thr Ser Asn Tyr Ala Asn
1               5                   10

<210> SEQ ID NO 17
```

```
<211> LENGTH: 7
<212> TYPE: PRT
<213> ORGANISM: Artificial Sequence
<220> FEATURE:
<223> OTHER INFORMATION: synthetic light chain CDR2 of clone 11

<400> SEQUENCE: 17

Gly Thr Asn Asn Arg Ala Pro
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic light chain CDR3 of clone 11

<400> SEQUENCE: 18

Ala Leu Trp Tyr Ser Asn His Trp Val
1               5

<210> SEQ ID NO 19
<211> LENGTH: 125
<212> TYPE: PRT
<213> ORGANISM: Artificial Sequence
<220> FEATURE:
<223> OTHER INFORMATION: synthetic heavy chain variable region of clone
      1

<400> SEQUENCE: 19

Gln Gly Gln Leu Gln Gln Ser Gly Ala Glu Leu Val Arg Pro Gly Ala
1               5                   10                  15

Ser Val Thr Leu Thr Cys Lys Ala Ser Gly Tyr Thr Phe Thr Asp Tyr
            20                  25                  30

Glu Met His Trp Val Lys Gln Thr Pro Ile His Gly Leu Glu Trp Ile
        35                  40                  45

Gly Val Ile Glu Ser Glu Thr Gly Gly Thr Ala Tyr Asn Gln Lys Phe
    50                  55                  60

Lys Gly Lys Ala Lys Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Glu Gly Ile Thr Thr Val Ala Thr Thr Tyr Tyr Trp Tyr Phe
            100                 105                 110

Asp Val Trp Gly Thr Gly Thr Thr Val Thr Val Ser Ser
        115                 120                 125

<210> SEQ ID NO 20
<211> LENGTH: 112
<212> TYPE: PRT
<213> ORGANISM: Artificial Sequence
<220> FEATURE:
<223> OTHER INFORMATION: synthetic light chain variable region of clone
      1

<400> SEQUENCE: 20

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45
```

```
Pro Glu Leu Leu Ile Tyr Lys Val Tyr Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
                100                 105                 110
```

<210> SEQ ID NO 21
<211> LENGTH: 125
<212> TYPE: PRT
<213> ORGANISM: Artificial Sequence
<220> FEATURE:
<223> OTHER INFORMATION: synthetic heavy chain variable region of clone
      10

<400> SEQUENCE: 21

```
Gln Val Gln Leu Gln Gln Ser Gly Ala Glu Leu Val Arg Pro Gly Ala
 1               5                  10                  15

Ser Val Thr Leu Ser Cys Lys Ala Ser Gly Tyr Thr Phe Thr Asp Tyr
                 20                  25                  30

Glu Met His Trp Val Lys Gln Thr Pro Val His Gly Leu Glu Trp Ile
             35                  40                  45

Gly Ala Ile Asp Pro Glu Thr Gly Gly Ala Ala Tyr Asn Gln Lys Phe
 50                  55                  60

Lys Gly Lys Ala Ile Leu Thr Ala Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Glu Gly Ile Thr Thr Ser Val Val Thr Tyr Tyr Trp Tyr Phe
                100                 105                 110

Asp Val Trp Gly Thr Gly Thr Thr Val Thr Val Ser Ser
            115                 120                 125
```

<210> SEQ ID NO 22
<211> LENGTH: 112
<212> TYPE: PRT
<213> ORGANISM: Artificial Sequence
<220> FEATURE:
<223> OTHER INFORMATION: synthetic light chain variable region of clone
      10

<400> SEQUENCE: 22

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Arg Ile
 65                  70                  75                  80

Ser Arg Val Glu Pro Glu Asp Leu Gly Val Tyr Tyr Cys Phe Gln Gly
                 85                  90                  95

Ser His Val Pro Leu Thr Phe Gly Ser Gly Thr Lys Leu Glu Ile Lys
                100                 105                 110
```

<210> SEQ ID NO 23
<211> LENGTH: 121
<212> TYPE: PRT
<213> ORGANISM: Artificial Sequence
<220> FEATURE:
<223> OTHER INFORMATION: synthetic heavy chain variable region of clone 11

<400> SEQUENCE: 23

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asn Thr Ser Lys Asn Gln Val
65                  70                  75                  80

Phe Leu Lys Ile Ala Asn Val Asp Thr Glu Asp Thr Ala Thr Tyr Tyr
                85                  90                  95

Cys Ala Arg Ile Glu Glu Arg Phe Arg Trp Tyr Phe Asp Val Trp Gly
            100                 105                 110

Thr Gly Thr Thr Val Thr Val Ser Ser
        115                 120
```

<210> SEQ ID NO 24
<211> LENGTH: 109
<212> TYPE: PRT
<213> ORGANISM: Artificial Sequence
<220> FEATURE:
<223> OTHER INFORMATION: synthetic light chain variable region of clone 11

<400> SEQUENCE: 24

```
Arg Ala Gly Trp Thr Gln Glu Ser Ala Leu Thr Thr Ser Pro Gly Glu
1               5                   10                  15

Thr Val Thr Leu Thr Cys Arg Ser Ser Thr Gly Ala Ile Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105
```

<210> SEQ ID NO 25
<211> LENGTH: 375
<212> TYPE: DNA
<213> ORGANISM: Artificial Sequence
<220> FEATURE:
<223> OTHER INFORMATION: synthetic heavy chain variable region of clone 1

<400> SEQUENCE: 25

```
cagggtcaac tgcagcagtc tggggctgag ctggtgaggc ctggggcttc agtgacgctg      60
```

```
acctgcaagg cttcgggcta cacatttact gactatgaaa tgcactgggt gaagcagaca    120
cctatacatg gcctggaatg gattggagtt attgaatctg aaactggtgg tactgcctac    180
aatcagaagt tcaagggcaa ggccaaactg actgcagaca atcctccag cacagcctac     240 atggagctcc gcagcctgac atctgaggac tctgccgtct attactgtac aagagagggt    300
attactacgg tagcaactac gtactactgg tacttcgatg tctggggcac agggaccacg    360
gtcaccgtct cctca                                                     375

<210> SEQ ID NO 26
<211> LENGTH: 336
<212> TYPE: DNA
<213> ORGANISM: Artificial Sequence
<220> FEATURE:
<223> OTHER INFORMATION: synthetic light chain variable region of clone
      1

<400> SEQUENCE: 26
gatgttttga tgacccagac tccactctcc ctgcctgtca gtcttggaga tcaagcctcc    60
atctcttgca gatctagtca gagcattgta catagtaatg aaacaccta tttagaatgg    120 tacctgcaga aaccaggcca gtctccagag ctcctgatct acaaagttta caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcca    300
ttcacgttcg gctcggggac aaagttggaa ataaaa                              336

<210> SEQ ID NO 27
<211> LENGTH: 375
<212> TYPE: DNA
<213> ORGANISM: Artificial Sequence
<220> FEATURE:
<223> OTHER INFORMATION: synthetic heavy chain variable region of clone
      10

<400> SEQUENCE: 27
caggttcaac tgcagcagtc tggggctgag ctggtgaggc ctggggcttc agtgacgctg    60
tcctgcaagg cttcgggcta cacatttact gactatgaaa tgcactgggt gaagcagaca    120
cctgtgcatg gcctggaatg gattggagct attgatcctg aaactggtgg tgctgcctac    180
aatcagaagt tcaagggcaa ggccatactg actgcagaca atcctccag cacagcctac     240 atggagctcc gcagcctgac atctgaggac tctgccgtct attactgtac aagagagggt    300
attactacgt cagtggttac gtactactgg tacttcgatg tctggggcac agggaccacg    360
gtcaccgtct cctca                                                     375

<210> SEQ ID NO 28
<211> LENGTH: 336
<212> TYPE: DNA
<213> ORGANISM: Artificial Sequence
<220> FEATURE:
<223> OTHER INFORMATION: synthetic light chain variable region of clone
      10

<400> SEQUENCE: 28
gatgttttga tgacccaaac tccactctcc ctgcctgtca gtcttggaga tcaagcctcc    60
atctcttgca gatctagtca gagcattgta catagtaatg aaacaccta tttagaatgg    120 tacctgcaga aaccaggcca gtctccaaag ctcctgatct acaaagtttc caaccgattt    180
tctggggtcc cagacaggtt cagtggcagt ggatcaggga cagatttcac actcaggatc    240
```
agcagagtgg agcctgagga tctgggagtt tattactgct ttcaaggttc acatgttcca      300
ctcacgttcg gctcggggac aaagttggaa ataaaa                                336

<210> SEQ ID NO 29
<211> LENGTH: 363
<212> TYPE: DNA
<213> ORGANISM: Artificial Sequence
<220> FEATURE:
<223> OTHER INFORMATION: synthetic heavy chain variable region of clone
      11

<400> SEQUENCE: 29
caggttactc tgaaagagtc tggccctggg atattgcagc cctcccagac cctcagtctg      60
acttgttctt tctctgggtt ttcactgagc acttttggta tgggtgtcgg ctggattcgt     120
cagccttcag ggaagggtct ggagtggctg gcacacattt ggtgggatga tgataagtac     180
tataatcccg ccctgaagag tcggctcaca atctccaaga atacctccaa aaaccaggta     240
ttcctcaaga tcgccaatgt ggacactgaa gatactgcca catactactg tgctcgaata     300
gaggagaggt tccgctggta cttcgatgtc tggggcacag gaccacggt caccgtctcc     360 tca                                                                   363

<210> SEQ ID NO 30
<211> LENGTH: 327
<212> TYPE: DNA
<213> ORGANISM: Artificial Sequence
<220> FEATURE:
<223> OTHER INFORMATION: synthetic light chain variable region of clone
      11

<400> SEQUENCE: 30
agggctggtt ggactcagga atctgcactc accacatcac ctggtgaaac agtcacactc      60
acttgtcgct caagtactgg ggctattaca actagtaact atgccaactg ggtccaagaa     120
aaaccagatc atttattcac tggtctaata ggtggtacca caaccgagc tccaggtgtt     180 cctgccagat tctcaggctc cctgattgga gacaaggctg ccctcaccat cacaggggca     240
cagactgagg atgaggcaat atatttctgt gctctatggt acagcaacca ctgggtgttc     300
ggtggaggaa ccaaactgac tgtccta                                         327

<210> SEQ ID NO 31
<211> LENGTH: 31
<212> TYPE: DNA
<213> ORGANISM: Artificial Sequence
<220> FEATURE:
<223> OTHER INFORMATION: synthetic forward primer

<400> SEQUENCE: 31
gtacgctagc caccatgcag atcccacagg c                                    31

<210> SEQ ID NO 32
<211> LENGTH: 29
<212> TYPE: DNA
<213> ORGANISM: Artificial Sequence
<220> FEATURE:
<223> OTHER INFORMATION: synthetic reverse primer

<400> SEQUENCE: 32
gatcctcgag ccaccagggt ttggaactg                                       29

<210> SEQ ID NO 33

<211> LENGTH: 125
<212> TYPE: PRT
<213> ORGANISM: Artificial Sequence
<220> FEATURE:
<223> OTHER INFORMATION: synthetic heavy chain variable region of clone 38

<400> SEQUENCE: 33

Gln Gly Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Ile His Gly Leu Glu Trp Ile
            35                  40                  45

Gly Val Ile Glu Ser Glu Thr Gly Thr Ala Tyr Asn Gln Lys Phe
        50                  55                  60

Lys Gly Arg Val Thr Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Thr Thr Val Ala Thr Thr Tyr Tyr Trp Tyr Phe
            100                 105                 110

Asp Val Trp Gly Gln Gly Thr Thr Val Thr Val Ser Ser
        115                 120                 125

<210> SEQ ID NO 34
<211> LENGTH: 112
<212> TYPE: PRT
<213> ORGANISM: Artificial Sequence
<220> FEATURE:
<223> OTHER INFORMATION: synthetic light chain variable region of Clone 38, 39, and 41

<400> SEQUENCE: 34

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 35
<211> LENGTH: 125
<212> TYPE: PRT
<213> ORGANISM: Artificial Sequence
<220> FEATURE:
<223> OTHER INFORMATION: synthetic heavy chain variable region of Clone 39 and 48

<400> SEQUENCE: 35

Gln Gly Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
            35                  40                  45

Gly Val Ile Glu Ser Glu Thr Gly Gly Thr Ala Tyr Asn Gln Lys Phe
        50                  55                  60

Lys Gly Arg Ala Lys Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Ile Thr Thr Val Ala Thr Thr Tyr Tyr Trp Tyr Phe
            100                 105                 110

Asp Val Trp Gly Gln Gly Thr Thr Val Thr Val Ser Ser
            115                 120                 125

<210> SEQ ID NO 36
<211> LENGTH: 125
<212> TYPE: PRT
<213> ORGANISM: Artificial Sequence
<220> FEATURE:
<223> OTHER INFORMATION: synthetic heavy chain variable region of clone
      41

<400> SEQUENCE: 36

Gln Gly Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
            35                  40                  45

Gly Val Ile Glu Ser Glu Thr Gly Gly Thr Ala Tyr Asn Gln Lys Phe
        50                  55                  60

Gln Gly Arg Val Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Ile Thr Thr Val Ala Thr Thr Tyr Tyr Trp Tyr Phe
            100                 105                 110

Asp Val Trp Gly Gln Gly Thr Leu Val Thr Val Ser Ser
            115                 120                 125

<210> SEQ ID NO 37
<211> LENGTH: 112
<212> TYPE: PRT
<213> ORGANISM: Artificial Sequence
<220> FEATURE:
<223> OTHER INFORMATION: synthetic light chain variable region of clone
      48

<400> SEQUENCE: 37

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gln Gly Thr Lys Leu Glu Ile Lys
            100                 105                 110

<210> SEQ ID NO 38
<211> LENGTH: 375
<212> TYPE: DNA
<213> ORGANISM: Artificial Sequence
<220> FEATURE:
<223> OTHER INFORMATION: synthetic nucleotide sequence of the heavy
      chain variable region of Clone 38

<400> SEQUENCE: 38
cagggccagc tggtgcagag cggcgccgag gtgaagaagc ccggcgccag cgtgaaggtg    60
agctgcaagg ccagcggcta caccttcacc gactacgaga tgcactgggt gagacaggcc   120
cccatccacg gcctggagtg gatcggcgtg atcgagagcg agaccggcgg caccgcctac   180
aaccagaagt tcaagggcag agtgaccatc accgccgaca agagcaccag caccgcctac   240
atggagctga gcagcctgag aagcgaggac accgccgtgt actactgcgc cagagagggc   300
atcaccaccg tggccaccac ctactactgg tacttcgacg tgtggggcca gggcaccacc   360
gtgaccgtga gcagc                                                    375

<210> SEQ ID NO 39
<211> LENGTH: 336
<212> TYPE: DNA
<213> ORGANISM: Artificial Sequence
<220> FEATURE:
<223> OTHER INFORMATION: synthetic nucleotide sequence of the light
      chain variable region of Clone 38, 39, and 41

<400> SEQUENCE: 39
gatgtggtga tgacccagag cccgctgagc ctgccggtga ccctgggcca gccggcgagc    60
attagctgcc gcagcagcca gagcattgtg catagcaacg gcaacaccta tctggaatgg   120
tatctgcaga aaccgggcca gagcccgcag ctgctgattt ataaagtgag caaccgcttt   180
agcggcgtgc cggatcgctt tagcggcagc ggcagcggca ccgatttt ac cctgaaaatt   240 agccgcgtgg aagcggaaga tgtgggcgtg tattattgct ttcagggcag ccatgtgccg   300
ctgacctttg gccagggcac caaactggaa attaaa                             336

<210> SEQ ID NO 40
<211> LENGTH: 375
<212> TYPE: DNA
<213> ORGANISM: Artificial Sequence
<220> FEATURE:
<223> OTHER INFORMATION: synthetic nucleotide sequence of the heavy
      chain variable region of Clone 39 and 48

<400> SEQUENCE: 40
cagggccagc tggtgcagag cggcgccgag gtgaagaagc ccggcgccag cgtgaaggtg    60
agctgcaagg ccagcggcta caccttcacc gactacgaga tgcactgggt gagacaggcc   120
cccggccagg gcctggagtg gatgggcgtg atcgagagcg agaccggcgg caccgcctac   180
aaccagaagt tcaagggcag agccaagatc accgccgaca agagcaccag caccgcctac   240
atggagctga gcagcctgag aagcgaggac accgccgtgt actactgcac cagagagggc   300
atcaccaccg tggccaccac ctactactgg tacttcgacg tgtggggcca gggcaccacc   360

```
gtgaccgtga gcagc                                               375
```

<210> SEQ ID NO 41
<211> LENGTH: 375
<212> TYPE: DNA
<213> ORGANISM: Artificial Sequence
<220> FEATURE:
<223> OTHER INFORMATION: synthetic nucleotide sequence of the heavy
      chain variable region of Clone 41

<400> SEQUENCE: 41

```
cagggccagc tggtgcagag cggcgcggaa gtgaaaaaac cgggcgcgag cgtgaaagtg    60
agctgcaaag cgagcggcta ccctttacc gattatgaaa tgcattgggt gcgccaggcg   120
ccgggccagg gcctggaatg gatgggcgtg attgaaagcg aaaccggcgg caccgcgtat   180
aaccagaaat ttcagggccg cgtgaccctg accgcggata aaagcagcag caccgcgtat   240
atggaactga gcagcctgcg cagcgaagat accgcggtgt attattgcac ccgcgaaggc   300
attaccaccg tggcgaccac ctattattgg tattttgatg tgtggggcca gggcaccctg   360
gtgaccgtga gcagc                                                    375
```

<210> SEQ ID NO 42
<211> LENGTH: 336
<212> TYPE: DNA
<213> ORGANISM: Artificial Sequence
<220> FEATURE:
<223> OTHER INFORMATION: synthetic nucleotide sequence of the light
      chain variable region of Clone 48

<400> SEQUENCE: 42

```
gatgtggtga tgacccagag cccgctgagc ctgccggtga ccctgggcca gccggcgagc    60
attagctgcc gcagcagcca gagcattgtg catagcaacg gcaacaccta tctggaatgg   120
tatctgcaga aaccgggcca gagcccgcgc ctgctgattt ataaagtgag caaccgcttt   180
agcggcgtgc cggatcgctt tagcggcagc ggcagcggca ccgatttac cctgaaaatt   240
agccgcgtgg aagcggaaga tgtgggcgtg tattattgct ttcagggcag ccatgtgccg   300
ctgacctttg gccagggcac caaactggaa attaaa                              336
```

<210> SEQ ID NO 43
<211> LENGTH: 288
<212> TYPE: PRT
<213> ORGANISM: Homo sapiens

<400> SEQUENCE: 43

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110
```

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Ile Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gly Pro Leu Arg Pro Glu Asp Gly His Cys Ser Trp Pro Leu
            275                 280                 285

<210> SEQ ID NO 44
<211> LENGTH: 288
<212> TYPE: PRT
<213> ORGANISM: Macaca fascicularis

<400> SEQUENCE: 44

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

Asn Ala Pro Thr Phe Ser Pro Ala Leu Leu Ile Val Thr Glu Gly Asp
        35                  40                  45

Asn Ala Thr Phe Thr Cys Ser Phe Ser Asn Ala Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro

```
            195                 200                 205
Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285

<210> SEQ ID NO 45
<211> LENGTH: 288
<212> TYPE: PRT
<213> ORGANISM: Mus musculus

<400> SEQUENCE: 45

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Met Ala Thr Phe Thr Cys Ser Leu Ser Asn Trp Ser Glu Ser Leu Met
    50                  55                  60

Leu Asn Trp Asn Tyr Leu Ser Pro Ser Asn Gln Thr Glu Leu Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Glu Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Cys Pro Ser Val Ala
    210                 215                 220

Tyr Glu Glu Leu Asp Phe Gly Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Arg Asp Gly His Cys Ser Trp Pro Leu
        275                 280                 285
```